(12) United States Patent
Funahashi

(10) Patent No.: US 8,614,009 B2
(45) Date of Patent: *Dec. 24, 2013

(54) AROMATIC AMINE DERIVATIVE AND ORGANIC ELECTROLUMINESCENT ELEMENT USING THE SAME

(75) Inventor: Masakazu Funahashi, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 938 days.

This patent is subject to a terminal disclaimer.

(21) Appl. No.: 11/912,768

(22) PCT Filed: Apr. 6, 2006

(86) PCT No.: PCT/JP2006/307370
§ 371 (c)(1),
(2), (4) Date: Oct. 26, 2007

(87) PCT Pub. No.: WO2006/117974
PCT Pub. Date: Nov. 9, 2006

(65) Prior Publication Data
US 2009/0072716 A1    Mar. 19, 2009

(30) Foreign Application Priority Data

Apr. 26, 2005 (JP) ................................. 2005-128653

(51) Int. Cl.
*H01L 51/54* (2006.01)
(52) U.S. Cl.
USPC ........... 428/690; 428/917; 313/504; 313/505; 313/506; 257/40; 257/E51.05; 257/E51.026; 257/E51.032; 564/20; 564/426; 564/434
(58) Field of Classification Search
USPC ................... 428/690, 917; 313/504, 505, 506; 564/426, 434, 26; 257/40, E51.05, 257/E51.026, E51.032
See application file for complete search history.

(56) References Cited

U.S. PATENT DOCUMENTS

| | | | |
|---|---|---|---|
| 5,141,671 A * | 8/1992 | Bryan et al. | 252/301.16 |
| 6,849,345 B2 * | 2/2005 | Parton et al. | 428/690 |
| 7,470,472 B2 * | 12/2008 | Funahashi | 428/690 |

(Continued)

FOREIGN PATENT DOCUMENTS

| | | |
|---|---|---|
| JP | 08 012600 | 1/1996 |
| JP | 8 305053 | 11/1996 |

(Continued)

OTHER PUBLICATIONS

So et al., PS-C21, The Seventh International Symposium on Functional Electron Systems (2007).*

(Continued)

*Primary Examiner* — Gregory Clark
(74) *Attorney, Agent, or Firm* — Oblon, Spivak, McClelland, Maier & Neustadt, L.L.P.

(57) ABSTRACT

The present invention provides an aromatic amine derivative having a specific structure including a substituted diphenylamino group attached to a naphthalene structure. This aromatic amine derivative can realize an organic electroluminescent element having high emission luminance and luminous efficiency and having a prolonged lifetime. The organic electroluminescent element includes an organic thin film layer provided between a cathode and an anode. The organic thin film layer has a single layer or multilayer structure including at least a light emitting layer. At least one layer in the organic thin film layer contains the aromatic amine derivative either solely or as a component of a mixture.

15 Claims, 3 Drawing Sheets

(56) References Cited

U.S. PATENT DOCUMENTS

| | | | |
|---|---|---|---|
| 7,834,214 B2 * | 11/2010 | Funahashi | 564/429 |
| 2005/0064233 A1 | 3/2005 | Matsuura et al. | |
| 2005/0214567 A1 | 9/2005 | Parton et al. | |
| 2006/0177693 A1 | 8/2006 | Funahashi | |
| 2006/0232194 A1 * | 10/2006 | Tung et al. | 313/504 |

FOREIGN PATENT DOCUMENTS

| | | | | |
|---|---|---|---|---|
| JP | 11 003782 | 1/1999 | | |
| JP | 11-236360 | 8/1999 | | |
| JP | 11-273860 | * 8/1999 | | C09K 9/02 |
| JP | 11 273860 | 10/1999 | | |
| JP | 2001 284050 | 10/2001 | | |
| JP | 2003-133076 | 5/2003 | | |
| JP | 2006-253445 | 9/2006 | | |
| WO | 94 06157 | 3/1994 | | |

OTHER PUBLICATIONS

Office Action issued Jan. 4, 2011, in Japan Patent Application No. 2005-128653.

* cited by examiner

AROMATIC AMINE DERIVATIVE AND ORGANIC ELECTROLUMINESCENT ELEMENT USING THE SAME

TECHNICAL FIELD

The present invention relates to a novel aromatic amine derivative and an organic electroluminescence (EL) device using the derivative, in particular, an organic EL device having high emission luminance, high luminous efficiency, and a long lifetime, and a novel aromatic amine derivative for realizing the device.

BACKGROUND ART

A large number of organic EL devices each using an organic substance have been developed because of their potential to find applications in solid light emission type, inexpensive, large-area, full-color display devices. In general, an EL device is constituted of a light emitting layer and a pair of opposing electrodes between which the layer is interposed. Light emission is the following phenomenon: when an electric field is applied between both the electrodes, an electron is injected from a cathode side and a hole is injected from an anode side, and, furthermore, the electron recombines with the hole in the light emitting layer to produce an excited state, and energy generated upon return of the excited state to a ground state is emitted as light.

A conventional organic EL device has been driven at a voltage higher than the voltage at which an inorganic light emitting diode is driven, and has had emission luminance and luminous efficiency lower than those of the diode. In addition, the properties of the device have deteriorated remarkably, so the device has not been put into practical use. Although a recent organic EL device has been gradually improved, additionally high luminous efficiency and an additionally long lifetime of the device are requested.

For example, a technology involving the use of a single monoanthracene compound as an organic light emitting material has been disclosed (Patent Document 1). However, the technology provides a luminance as low as 1,650 cd/m$^2$ at a current density of, for example, 165 mA/cm$^2$, and provides extremely low efficiency, specifically, 1 cd/A, so the technology is not practical. In addition, a technology involving the use of a single bisanthracene compound as an organic light emitting material has been disclosed (Patent Document 2). However, even the technology provides an efficiency as low as about 1 to 3 cd/A, so an improvement for putting the technology into practical use has been demanded. Meanwhile, a long-lifetime organic EL device obtained by adding, for example, styrylamine to a distyryl compound to be used as an organic light emitting material has been proposed (Patent Document 3). However, the device does not have a sufficient half-lifetime, and the additional improvement of the device has been demanded.

In addition, technologies each involving the use of each of a monoanthracene or bisanthracene compound and a distyryl compound in an organic light emitting medium layer have been disclosed (Patent Document 4). However, in each of those technologies, the conjugate structure of the styryl compound lengthens the wavelength of an emission spectrum, with the result that a color purity is deteriorated. Further, a device using a diaminonaphthalene compound as an emitting layer has been disclosed (Patent Document 5). However, the device does not have a sufficient half-lifetime, and the additional improvement of the device has been demanded.

Patent Document 1: JP 11-3782 A
Patent Document 2: JP 8-12600 A
Patent Document 3: WO 94/06157
Patent Document 4: JP 2001-284050 A
Patent Document 5: JP 11-273860 A

DISCLOSURE OF THE INVENTION

Problem to be Solved by the Invention

The present invention has been made with a view to solving the above problems, and an object of the present invention is to provide an organic EL device having high emission luminance, high luminous efficiency, and a long lifetime, and a novel aromatic amine derivative for realizing the device.

Means for Solving the Problem

The inventors of the present invention have made extensive studies with a view to developing an aromatic amine derivative having the above preferable nature and an organic EL device using the derivative. As a result, the inventors have found that the utilization of an aromatic amine derivative represented by any one of the following general formulae (1) to (7) in which a diphenylamino group having a substituent is bonded to a naphthalene structure can achieve the object. The present invention has been completed on the basis of such finding.

In other words, the present invention provides an aromatic amine derivative represented by any one of the following general formulae (1) to (7):

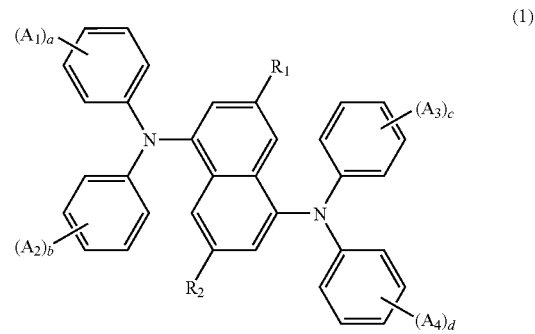

(1)

in the general formula (1): $R_1$ and $R_2$ each independently represent a substituted or unsubstituted aryl group having 5 to 50 carbon atoms, a substituted or unsubstituted aralkyl group having 1 to 50 carbon atoms, a substituted or unsubstituted cycloalkyl group having 3 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted heterocyclic group having to 50 carbon atoms, a cyano group, or a halogen atom;

$A_1$ to $A_4$ each independently represent a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 3 to 50 carbon atoms, a substituted or unsubstituted alkoxyl group having 1 to 50 carbon atoms, a substituted or unsubstituted aryloxy group having 5 to 50 carbon atoms, a substituted or unsubstituted arylamino group having 5 to 50 carbon atoms, a substituted or unsubstituted alkylamino group having 1 to 20 carbon atoms, a substituted or unsubstituted heterocyclic group having 5 to 50 carbon atoms, or a halogen atom; and a to d each independently represent an integer of 0 to 5, and, when each one of a to d represents 2 or more, $A_1$s, $A_2$s, $A_3$s, or $A_4$s may be identical to or different from each other, or may be coupled with each other to form a saturated or unsaturated ring, and $A_1$ and $A_2$, or $A_3$ and $A_4$ may be coupled with each other to form a saturated or unsaturated ring, provided that a case where a substituent in each group represented by any one of $A_1$ to $A_4$ includes a group containing a vinyl group is excluded, and a case where all of $A_1$ to $A_4$ each represent a hydrogen atom is excluded;

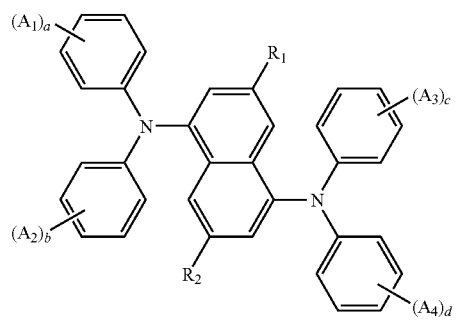

(2)

in the general formula (2), $R_1$, $R_2$, $A_1$ to $A_4$, and a to d each have the same meaning as that in the general formula (1), provided that a case where a substituent in each group represented by any one of $A_1$ to $A_4$ includes a group containing a vinyl group is excluded, and at least one of $A_1$ to $A_4$ represents a substituted or unsubstituted, secondary or tertiary alkyl group having 3 to 10 carbon atom;

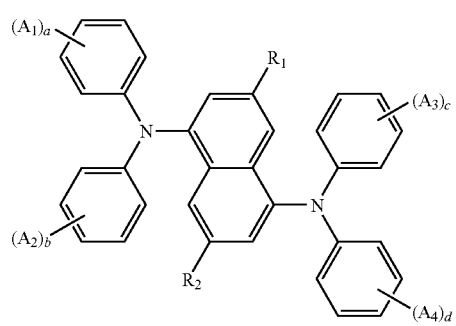

(3)

in the general formula (3), $R_1$, $R_2$, $A_1$ to $A_4$, and a to d each have the same meaning as that in the general formula (1), provided that a case where a substituent in each group represented by any one of $A_1$ to $A_4$ includes a group containing a vinyl group is excluded, and at least one of $A_1$ to $A_4$ represents an integer of 2 or more;

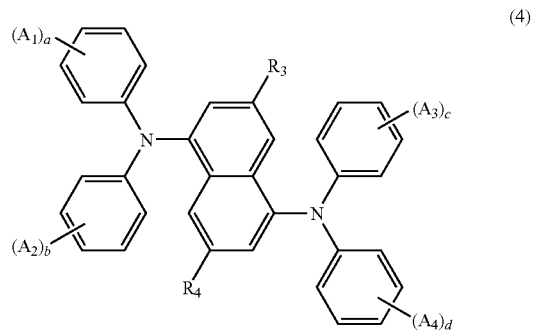

(4)

in the general formula (4): $R_3$ and $R_4$ each independently represent a hydrogen atom or an alkyl group having 1 to 20 carbon atoms provided that a case where both $R_3$ and $R_4$ each represent a hydrogen atom is excluded; and $A_1$ to $A_4$, and a to d each have the same meaning as that in the general formula (1), provided that a case where a substituent in each group represented by any one of $A_1$ to $A_4$ includes a group containing a vinyl group is excluded, and a case where all of $A_1$ to $A_4$ each represent a hydrogen atom is excluded;

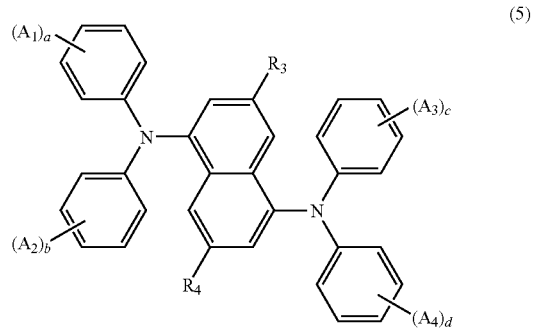

(5)

in the general formula (5), $R_3$, $R_4$, $A_1$ to $A_4$, and a to d each have the same meaning as that in the general formula (4), provided that a case where a substituent in each group represented by any one of $A_1$ to $A_4$ includes a group containing a vinyl group is excluded, and at least one of $A_1$ to $A_4$ represents a substituted or unsubstituted, secondary or tertiary alkyl group having 3 to 10 carbon atom;

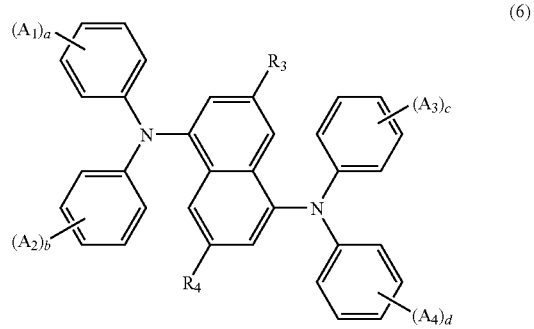

(6)

in the general formula (6), $R_3$, $R_4$, $A_1$ to $A_4$, and a to d each have the same meaning as that in the general formula (4), provided that a case where a substituent in each group represented by any one of $A_1$ to $A_4$ includes a group containing a vinyl group is excluded, and at least one of a to d represents an integer of 2 or more; and

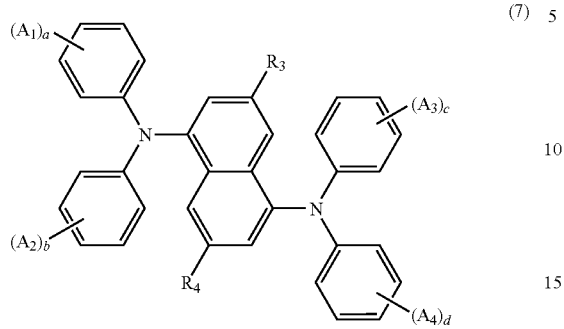

(7)

in the general formula (7), $R_3$, $R_4$, $A_1$ to $A_4$, and a to d each have the same meaning as that in the general formula (4), provided that a case where a substituent in each group represented by any one of $A_1$ to $A_4$ includes a group containing a vinyl group is excluded, and, when each one of a to d represents 2 or more, and $A_1$s, $A_2$s, $A_3$s, or $A_4$s are coupled with each other to form a saturated ring, a total number of carbon atoms in the ring is 12 or less.

Further, the present invention also provides: an organic EL device including an organic thin film layer composed of one or more layers including at least a light emitting layer and interposed between a cathode and an anode, in which at least one layer of the organic thin film layer contains the aromatic amine derivative alone or as a component of a mixture; and an organic EL device including an organic thin film layer composed of one or more layers including at least a light emitting layer and interposed between a cathode and an anode, in which an organic layer containing the aromatic amine derivative as a main component is present between the anode and the light emitting layer.

Effects of the Invention

An organic EL device using the aromatic amine derivative represented by any one of the general formulae (1) to (7) of the present invention has high emission luminance and high luminous efficiency, hardly deteriorates even after long-term use, and has a long lifetime.

BEST MODE FOR CARRYING OUT THE INVENTION

Figure 1:
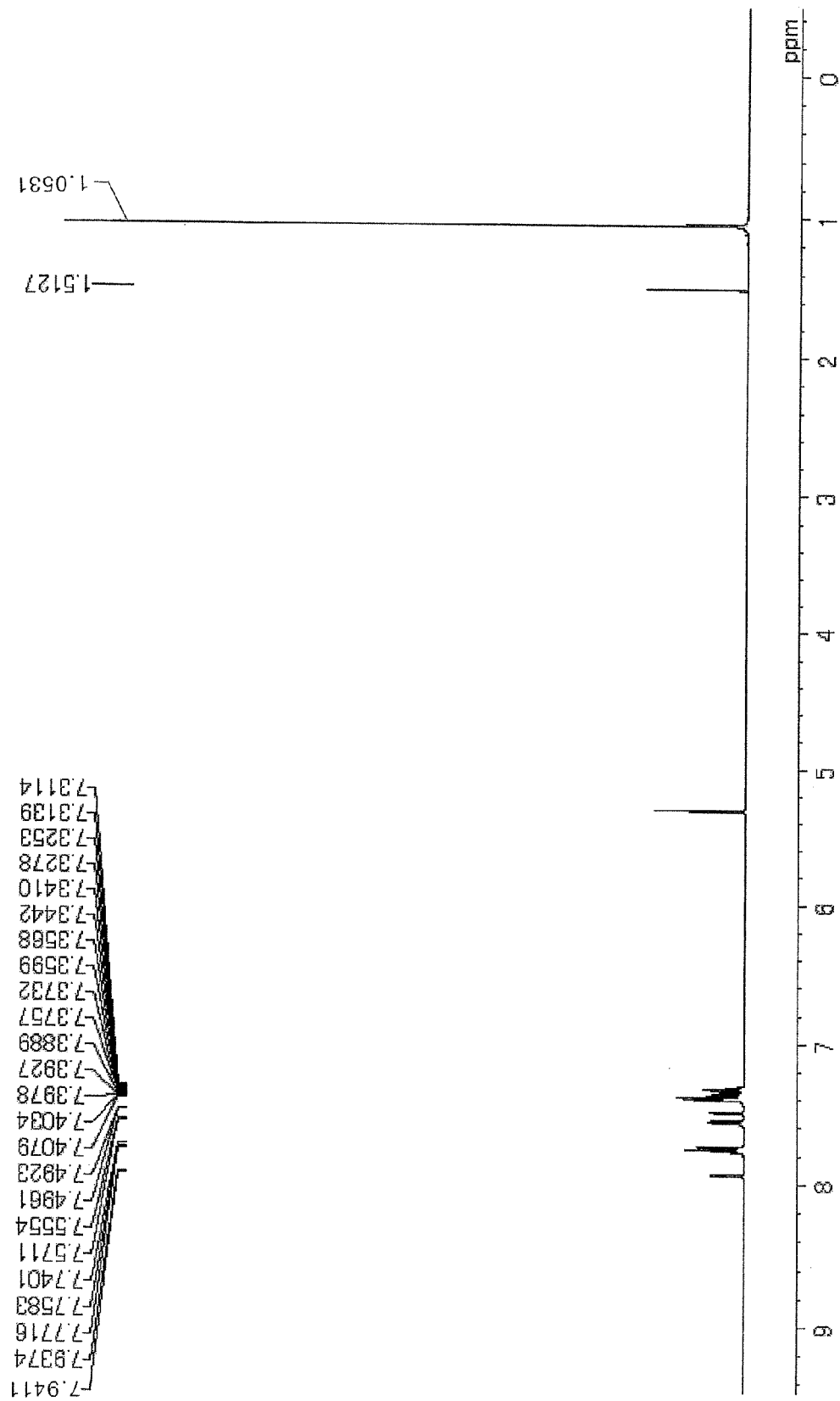
FIG. 1 is a view showing the NMR spectrum of Compound (D-66) as an aromatic amine derivative of the present invention.

An aromatic amine derivative of the present invention is composed of an aromatic amine derivative represented by any one of the following general formulae (1) to (7).

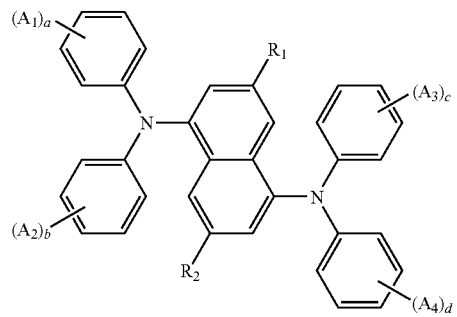

(1)

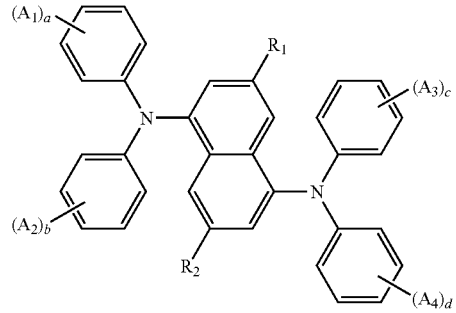

(2)

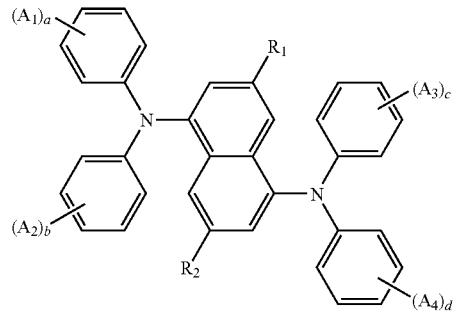

(3)

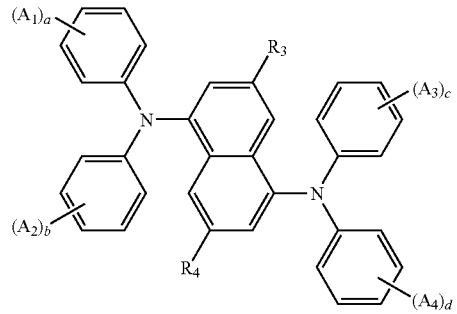

(4)

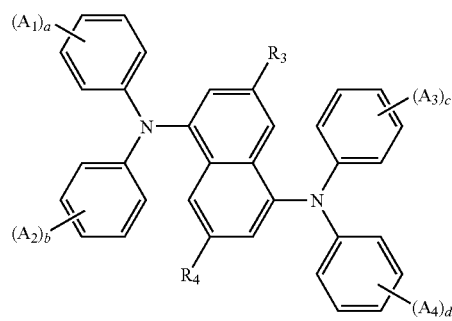

(5)

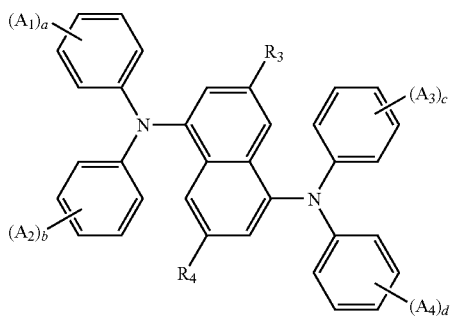

(6)

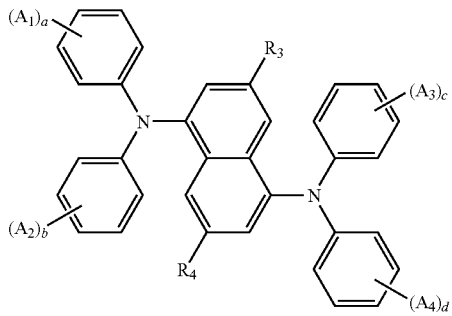

(7)

In each of the general formulae (1) to (3), $R_1$ and $R_2$ represent a substituted or unsubstituted aryl group having 5 to 50 carbon atoms (preferably 5 to 20 carbon atoms), a substituted or unsubstituted aralkyl group having 1 to 50 carbon atoms (preferably 9 to 20 carbon atoms), a substituted or unsubstituted cycloalkyl group having 3 to 50 carbon atoms (preferably 5 to 12 carbon atoms), a substituted or unsubstituted alkoxyl group having 1 to 50 carbon atoms (preferably 1 to 6-carbon atoms), a substituted or unsubstituted aryloxy group having 5 to 50 carbon atoms (preferably 5 to 18 carbon atoms), a substituted or unsubstituted arylamino group having 5 to 50 carbon atoms (preferably 5 to 18 carbon atoms), a substituted or unsubstituted alkylamino group having 1 to 20 carbon atoms (preferably 1 to 6 carbon atoms), or a halogen atom.

Examples of the aryl group represented by $R_1$ and $R_2$ above include a phenyl group, a 2-methylphenyl group, a 3-methylphenyl group, a 4-methylphenyl group, a 4-ethylphenyl group, a biphenyl group, a 4-methylbiphenyl group, a 4-ethylbiphenyl group, a 4-cyclohexylbiphenyl group, a terphenyl group, a 3,5-dichlorophenyl group, a naphthyl group, 5-methylnaphthyl group, an anthryl group, and a pyrenyl group.

Examples of the aralkyl group represented by $R_1$ and $R_2$ above include a benzyl group, a 1-phenylethyl group, a 2-phenylethyl group, a 1-phenylisopropyl group, a 2-phenylisopropyl group, a phenyl-t-butyl group, an α-naphtylmethyl group, a 1-α-naphtylethyl group, a 2-α-naphtylethyl group, a 1-α-naphthylisopropyl group, a 2-α-naphthylisopropyl group, a β-naphtylmethyl group, a 1-β-naphtylethyl group, a 2-β-naphtylethyl group, a 1-β-naphthylisopropyl group, a 2-β-naphthylisopropyl group, a 1-pyrrolylmethyl group, a 2-(1-pyrrolyl)ethyl group, a p-methylbenzyl group, a m-methylbenzyl group, an o-methylbenzyl group, a p-chlorobenzyl group, a m-chlorobenzyl group, an o-chlorobenzyl group, a p-bromobenzyl group, a m-bromobenzyl group, an o-bromobenzyl group, a p-iodobenzyl group, a m-iodobenzyl group, an o-iodobenzyl group, a p-hydroxybenzyl group, a m-hydroxybenzyl group, an o-hydroxybenzyl group, a p-aminobenzyl group, a m-aminobenzyl group, an o-aminobenzyl group, a p-nitrobenzyl group, am-nitrobenzyl group, an o-nitrobenzyl group, a p-cyanobenzyl group, a m-cyanobenzyl group, an o-cyanobenzyl group, a 1-hydroxy-2-phenylisopropyl group, and a 1-chloro-2-phenylisopropyl group.

Examples of the cycloalkyl group represented by $R_1$ and $R_2$ above include a cyclopropyl group, a cyclobutyl group, a cyclopentyl group, a cyclohexyl group, a norbornene group, and an adamantyl group.

Examples of the alkoxyl group represented by $R_1$ and $R_2$ above include a methoxy group, an ethoxy group, a propoxy group, an isopropoxy group, a butoxy group, an isobutoxy group, an s-butoxy group, a t-butoxy group, each kinds of pentyloxy groups, and each of hexyloxy groups.

Examples of the aryloxy group represented by $R_1$ and $R_2$ above include a phenoxy group, a tolyloxy group, and a naphthyloxy group.

Examples of the arylamino group represented by $R_1$ and $R_2$ above include a diphenylamino group, a ditolylamino group, an isopropyldiphenylamino group, t-butyldiphenylamino group, a diisopropyl diphenylamino group, a di-t-butyldiphenylamino group, a dinaphthylamino group, and a naphthylphenylamino group.

Examples of the alkylamino group represented by $R_1$ and $R_2$ above include a dimethylamino group, a diethylamino group, and a dihexylamino group.

Examples of the halogen atom represented by $R_1$ and $R_2$ above include a fluorine atom, a chlorine atom, and a bromine atom.

In each of the general formulae (4) to (7), $R_3$ and $R_4$ each represent a hydrogen atom, or a substituted or unsubstituted alkyl group having 1 to 50 carbon atoms (preferably 1 to 20 carbon atoms).

Examples of the alkyl group represented by $R_3$ and $R_4$ above include a methyl group, an ethyl group, a propyl group, an isopropyl group, a butyl group, an s-butyl group, a t-butyl group, a pentyl group, a hexyl group, a heptyl group, an octyl group, a stearyl group, a 2-phenylisopropyl group, a trichloromethyl group, a trifluoromethyl group, a benzyl group, an α-phenoxybenzyl group, an α,α-dimethylbenzyl group, an α,α-methylphenylbenzyl group, an α,α-ditrifluoromethylbenzyl group, a triphenylmethyl group, and an α-benzyloxybenzyl group.

Of the above alkyl groups, a methyl group, an ethyl group, a propyl group, an isopropyl group, a butyl group, an s-butyl group, or a t-butyl is preferable, or a methyl group, an ethyl group, a propyl group, or an isopropyl group is more preferable for each of $R_3$ and $R_4$.

In each of the general formulae (1) to (7), $A_1$ to $A_4$ each independently represent a hydrogen atom, a substituted or unsubstituted alkyl group having 1 to 50 carbon atoms (preferably 1 to 20 carbon atoms), a substituted or unsubstituted aryl group having 5 to 50 carbon atoms (preferably 5 to 20 carbon atoms), a substituted or unsubstituted aralkyl group having 1 to 50 carbon atoms (preferably 9 to 20 carbon atoms), a substituted or unsubstituted cycloalkyl group having 3 to 50 carbon atoms (preferably 5 to 12 carbon atoms), a substituted or unsubstituted alkoxyl group having 1 to 50 carbon atoms (preferably 1 to 6 carbon atoms), a substituted or unsubstituted aryloxy group having 5 to 50 carbon atoms (preferably 5 to 18 carbon atoms), a substituted or unsubstituted arylamino group having 5 to 50 carbon atoms (preferably 5 to 18 carbon atoms), a substituted or unsubstituted alkylamino group having 1 to 20 carbon atoms (preferably 1 to 6 carbon atoms), or a halogen atom.

Of those, a hydrogen atom, a substituted or unsubstituted alkyl group having 1 to 10 carbon atoms, a substituted or unsubstituted aryl group having 5 to 20 carbon atoms, a substituted or unsubstituted aralkyl group having 1 to 20 carbon atoms, or a substituted or unsubstituted cycloalkyl group having 3 to 10 carbon atoms is preferable, and a hydrogen atom, a substituted or unsubstituted alkyl group having 1 to 4 carbon atoms, a substituted or unsubstituted aryl group having 5 to 18 carbon atoms, a substituted or unsubstituted aralkyl group having 1 to 18 carbon atoms, or a substituted or unsubstituted cycloalkyl group having 3 to 6 carbon atoms is more preferable.

Specific examples of each of the alkyl group, the aryl group, the aralkyl group, the cycloalkyl group, the alkoxyl group, the aryloxy group, the arylamino group, the alkylamino group, and the halogen atom represented by any one of $A_1$ to $A_4$ include examples similar to those described for $R_1$ and $R_2$ described above.

a to d each represent an integer of 0 to 5, preferably 0 to 3, or more preferably 0 to 2.

When each one of a to d represents 2 or more, multiple $A_1$s, multiple $A_2$s, multiple $A_3$s, or multiple $A_4$s may be identical to or different from each other, or may be coupled with each other to form a saturated or unsaturated ring. In addition, $A_1$ and $A_2$, or $A_3$ and $A_4$ may be coupled with each other to form a saturated or unsaturated ring.

It should be noted that, in the general formula (1), the case where a substituent in each group represented by any one of $A_1$ to $A_4$ is a group containing a vinyl group is excluded, and the case where all of $A_1$ to $A_4$ each represent a hydrogen atom is excluded.

In addition, in the general formula (2), the case where a substituent in each group represented by any one of $A_1$ to $A_4$ is a group containing a vinyl group is excluded, and at least one of $A_1$ to $A_4$ represents a substituted or unsubstituted, secondary or tertiary alkyl group having 3 to 10 carbon atoms.

In addition, in the general formula (3), the case where a substituent in each group represented by any one of $A_1$ to $A_4$ is a group containing a vinyl group is excluded, and at least one of a to d represents an integer of 2 or more.

In addition, in the general formula (4), the case where a substituent in each group represented by any one of $A_1$ to $A_4$ is a group containing a vinyl group is excluded, and the case where all of $A_1$ to $A_4$ each represent a hydrogen atom is excluded.

In addition, in the general formula (5), the case where a substituent in each group represented by any one of $A_1$ to $A_4$ is a group containing a vinyl group is excluded, and at least one of $A_1$ to $A_4$ represents a substituted or unsubstituted, secondary or tertiary alkyl group having 3 to 10 carbon atoms.

In addition, in the general formula (6), the case where a substituent in each group represented by any one of $A_1$ to $A_4$ is a group containing a vinyl group is excluded, and at least one of a to d represents an integer of 2 or more.

In addition, in the general formula (7), the case where a substituent in each group represented by any one of $A_1$ to $A_4$ is a group containing a vinyl group is excluded, and, when each one of a to d represents 2 or more, and $A_1$s, $A_2$s, $A_3$s, or $A_4$s are coupled with each other to form a saturated ring, the total number of carbon atoms in the ring is 12 or less.

Specific examples of the aromatic amine derivative represented by any one of the general formulae (1) to (7) of the present invention are shown below. However, the present invention is not limited to these exemplified compounds. Me represents a methyl group.

| | $R_1$ | $R_2$ | (A₁)a | 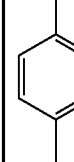(A₂)b | (A₃)c | 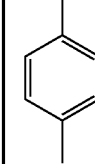(A₄)d |
|---|---|---|---|---|---|---|
| D-1 | Ethyl | Ethyl |  |  |  | 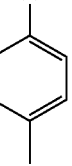 |
| D-2 | Ethyl | Ethyl |  |  | 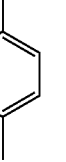 |  |
| D-3 | Ethyl | Ethyl |  |  |  | 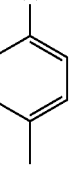 |
| D-4 | Ethyl | Ethyl | 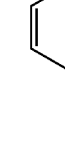 | 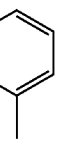 | 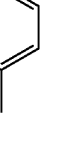 |  |
| D-5 | Ethyl | Ethyl |  |  |  | 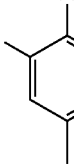 |
| D-6 | Ethyl | Ethyl | 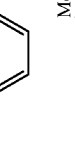 | 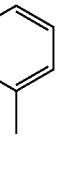 | |  |
| D-7 | Ethyl | Ethyl | | | | 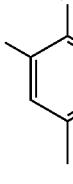 |

-continued

| | R₁ | R₂ | (A₁)a | (A₂)b | (A₃)c | (A₄)d |
|---|---|---|---|---|---|---|
| D-8 | Ethyl | Ethyl | 4-methylphenyl-CHMe₂ | 3,5-dimethylphenyl | 4-methylphenyl-CHMe₂ | 3,5-dimethylphenyl |
| D-9 | Ethyl | Ethyl | 4-methylphenyl-CHMe₂ | 4-methylphenyl-CHMe₂ | 4-methylphenyl-CHMe₂ | 4-methylphenyl-CHMe₂ |
| D-10 | Ethyl | Ethyl | 4-methylphenyl-CMe₃ | 4-methylphenyl-CMe₃ | 4-methylphenyl-CMe₃ | 4-methylphenyl-CMe₃ |
| D-11 | Ethyl | Ethyl | phenyl | 4-methylphenyl-CHMe | phenyl | 4-methylphenyl-CHMe |
| D-12 | Ethyl | Ethyl | 4-methylphenyl | 4-methylphenyl-CHMe | 4-methylphenyl | 4-methylphenyl-CHMe |
| D-13 | Ethyl | Ethyl | 4-methylphenyl-CHMe₂ | 4-cyclohexylphenyl | 4-methylphenyl-CHMe₂ | 4-cyclohexylphenyl |
| D-14 | Ethyl | Ethyl | 3,5-dimethylphenyl | 3,5-dimethylphenyl | 3,5-dimethylphenyl | 3,5-dimethylphenyl |

-continued

| | R₁ | R₂ | (A₁)a | (A₂)b | (A₃)c | (A₄)d |
|---|---|---|---|---|---|---|
| D-15 | Ethyl | Ethyl | 4-methylphenyl | 4-biphenyl | phenyl | 4-biphenyl |
| D-16 | Ethyl | Ethyl | phenyl | 6-methyl-2-naphthyl | phenyl | 6-methyl-2-naphthyl |
| D-17 | Ethyl | Ethyl | 6-methyl-2-naphthyl | 6-methyl-2-naphthyl | 6-methyl-2-naphthyl | 6-methyl-2-naphthyl |
| D-18 | Ethyl | Ethyl | 4-biphenyl | 4-biphenyl | 4-biphenyl | 4-biphenyl |
| D-19 | Isopropyl | Isopropyl | 4-(2-methyl-2-propyl)phenyl | 6-methyl-2-naphthyl | 4-(2-methyl-2-propyl)phenyl | 6-methyl-2-naphthyl |
| D-20 | Isopropyl | Isopropyl | phenyl | 4-methylphenyl | phenyl | 4-methylphenyl |
| D-21 | Isopropyl | Isopropyl | phenyl | 3-methylphenyl | phenyl | 3-methylphenyl |
| D-22 | Isopropyl | Isopropyl | phenyl | 4-(1-methylethyl)phenyl | phenyl | 4-(1-methylethyl)phenyl |

-continued
| | $R_1$ | $R_2$ | $(A_1)a$ | $(A_2)b$ | $(A_3)c$ | $(A_4)d$ |
|---|---|---|---|---|---|---|
| D-23 | Isopropyl | Isopropyl | 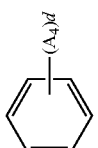 | 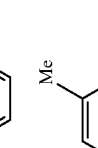 | 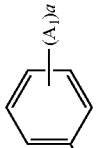 | 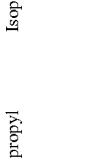 |
| D-24 | Isopropyl | Isopropyl | 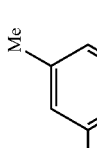 | 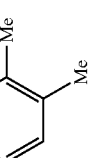 | 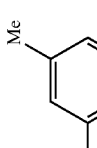 | 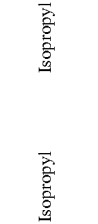 |
| D-25 | Isopropyl | Isopropyl | 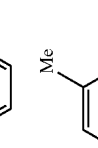 | 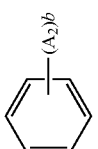 | 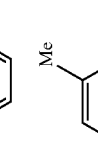 |  |
| D-26 | Isopropyl | Isopropyl | 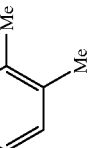 | 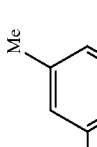 | 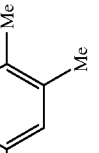 |  |
| D-27 | Isopropyl | Isopropyl | 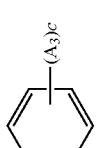 | 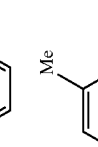 |  |  |
| D-28 | Isopropyl | Isopropyl | 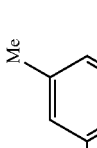 | 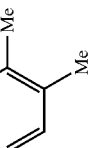 | |  |
| D-29 | Isopropyl | Isopropyl | | | |  |

-continued
| | $R_1$ | $R_2$ | $(A_1)a$ | $(A_2)b$ | $(A_3)c$ | $(A_4)d$ |
|---|---|---|---|---|---|---|
| D-30 | Isopropyl | Isopropyl | 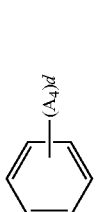 | 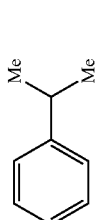 | 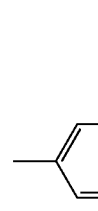 | 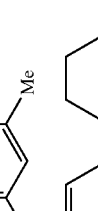 |
| D-31 | Isopropyl | Isopropyl | 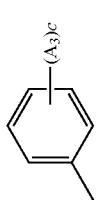 | 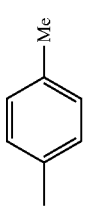 | 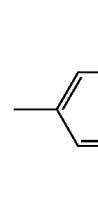 | 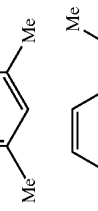 |
| D-32 | Isopropyl | Isopropyl | 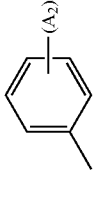 | 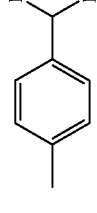 | 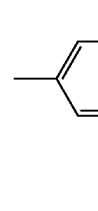 | 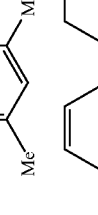 |
| D-33 | Isopropyl | Isopropyl | | | | |
| D-34 | Isopropyl | Isopropyl | | | | |
| D-35 | Isopropyl | Isopropyl | | | | |
| D-36 | Isopropyl | Isopropyl | | | | |
| D-37 | Isopropyl | Isopropyl | | | | |

-continued

| | R₁ | R₂ | (A₁)a | (A₂)b | (A₃)c | (A₄)d |
|---|---|---|---|---|---|---|
| D-38 | Isopropyl | Isopropyl | phenyl (m-tolyl) | 2-methylnaphthyl | phenyl (m-tolyl) | 2-methylnaphthyl |
| D-39 | Isopropyl | Isopropyl | 2-methylnaphthyl | 2-methylnaphthyl | 2-methylnaphthyl | 2-methylnaphthyl |
| D-40 | Isopropyl | Isopropyl | 6-isopropyl-2-methylnaphthyl | 2-methylnaphthyl | 6-isopropyl-2-methylnaphthyl | 6-isopropyl-2-methylnaphthyl |
| D-41 | Isopropyl | Isopropyl | 4-isopropylphenyl | 2-methylnaphthyl | 4-isopropylphenyl | 2-methylnaphthyl |
| D-42 | Isopropyl | Isopropyl | 4-tert-butylphenyl | 2-methylnaphthyl | 4-tert-butylphenyl | 2-methylnaphthyl |
| D-43 | Isopropyl | Isopropyl | phenyl (m-tolyl) | phenyl (m-tolyl) | phenyl (m-tolyl) | m-tolyl |
| D-44 | Isopropyl | Isopropyl | phenyl (m-tolyl) | phenyl (m-tolyl) | phenyl (m-tolyl) | 2-methylnaphthyl |

-continued
| | $R_1$ | $R_2$ | $(A_1)a$ | $(A_2)b$ | $(A_3)c$ | $(A_4)d$ |
|---|---|---|---|---|---|---|
| D-45 | Isopropyl | Isopropyl | 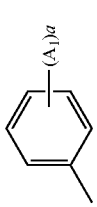 | 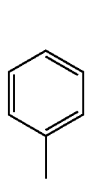 | 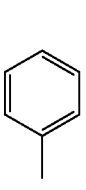 | 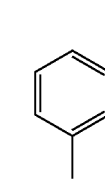 |
| D-46 | Isopropyl | Isopropyl | 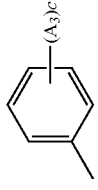 | 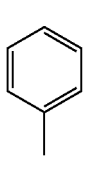 | 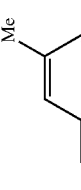 | 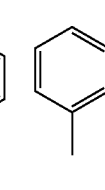 |
| D-47 | sec-Butyl | sec-Butyl | 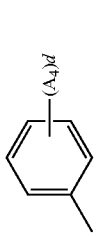 | | | |
| D-48 | sec-Butyl | sec-Butyl | 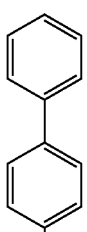 | 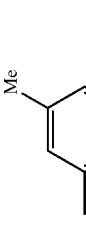 | 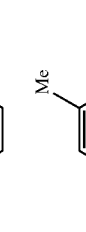 | 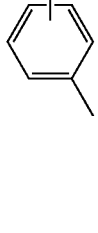 |
| D-49 | sec-Butyl | sec-Butyl |  |  |  | 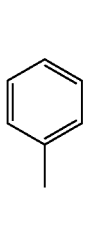 |
| D-50 | sec-Butyl | sec-Butyl | 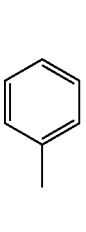 | 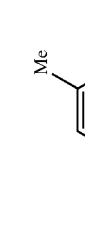 |  |  |

| | $R_1$ | $R_2$ | (A₁)a | (A₂)b | (A₃)c | (A₄)d |
|---|---|---|---|---|---|---|
| D-51 | sec-Butyl | sec-Butyl | 3,5-diMe-C₆H₃ | 3,5-diMe-C₆H₃ | 3,5-diMe-C₆H₃ | 3,5-diMe-C₆H₃ |
| D-52 | sec-Butyl | sec-Butyl | 4-Me-C₆H₄ | 4-Me-C₆H₄ | 4-Me-C₆H₄ | 4-Me-C₆H₄ |
| D-53 | sec-Butyl | sec-Butyl | 4-(CH₂Me)-C₆H₄ | 4-(CH₂Me)-C₆H₄ | 4-(CH₂Me)-C₆H₄ | 4-(CH₂Me)-C₆H₄ |
| D-54 | sec-Butyl | sec-Butyl | 4-(CHMe₂)-C₆H₄ | 4-(CHMe₂)-C₆H₄ | 4-(CHMe₂)-C₆H₄ | 4-(CHMe₂)-C₆H₄ |
| D-55 | tert-Butyl | tert-Butyl | 4-(CMe₃)-C₆H₄ | 2-naphthyl | 4-(CMe₃)-C₆H₄ | 2-naphthyl |
| D-56 | tert-Butyl | tert-Butyl | C₆H₅ | 3-Me-C₆H₄ | C₆H₅ | 3-Me-C₆H₄ |
| D-57 | tert-Butyl | tert-Butyl | 3-Me-C₆H₄ | 3-Me-C₆H₄ | 3-Me-C₆H₄ | 3-Me-C₆H₄ |

-continued
| | $R_1$ | $R_2$ | $(A_1)a$ | $(A_2)b$ | $(A_3)c$ | $(A_4)d$ |
|---|---|---|---|---|---|---|
| D-58 | tert-Butyl | tert-Butyl | 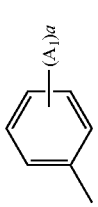 | 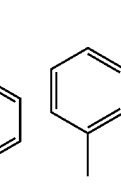 | 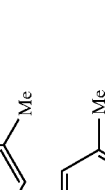 | 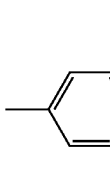 |
| D-59 | tert-Butyl | tert-Butyl | 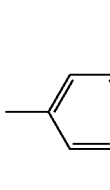 | 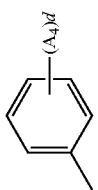 | 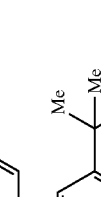 | 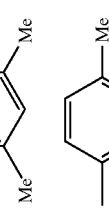 |
| D-60 | tert-Butyl | tert-Butyl | 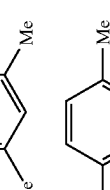 | 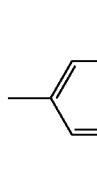 | 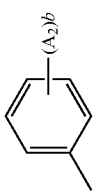 | 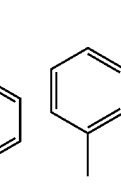 |
| D-61 | tert-Butyl | tert-Butyl | 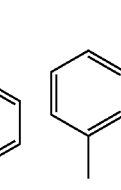 | 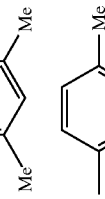 | 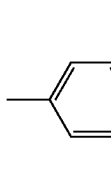 | 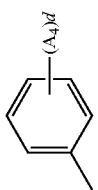 |
| D-62 | tert-Butyl | tert-Butyl | 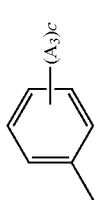 | 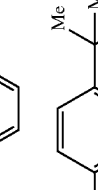 | 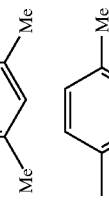 | 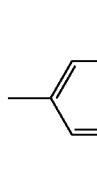 |
| D-63 | tert-Butyl | tert-Butyl | 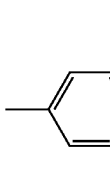 |  | 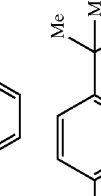 | 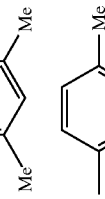 |
| D-64 | tert-Butyl | tert-Butyl | 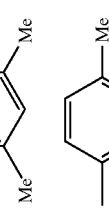 |  | 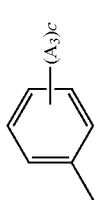 | 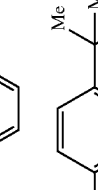 |

-continued

| | $R_1$ | $R_2$ | $(A_1)a$ | $(A_2)b$ | $(A_3)c$ | $(A_4)d$ |
|---|---|---|---|---|---|---|
| D-65 | tert-Butyl | tert-Butyl | 3,5-dimethylphenyl | 3,5-dimethylphenyl | 3,5-dimethylphenyl | 3,5-dimethylphenyl |
| D-66 | tert-Butyl | tert-Butyl | 6-methylnaphthalen-2-yl | 6-methylnaphthalen-2-yl | 6-methylnaphthalen-2-yl | 6-methylnaphthalen-2-yl |
| D-67 | tert-Butyl | tert-Butyl | 4-isopropylphenyl | 3,5-dimethylphenyl | 4-isopropylphenyl | 3,5-dimethylphenyl |
| D-68 | tert-Butyl | tert-Butyl | 4-isopropylphenyl | 4-isopropylphenyl | 4-isopropylphenyl | 4-isopropylphenyl |
| D-69 | tert-Butyl | tert-Butyl | 4-tert-butylphenyl | 4-tert-butylphenyl | 4-tert-butylphenyl | 4-tert-butylphenyl |
| D-70 | tert-Butyl | tert-Butyl | phenyl | 4-isopropylphenyl | phenyl | 4-isopropylphenyl |
| D-71 | tert-Butyl | tert-Butyl | 4-methylphenyl | 4-isopropylphenyl | 4-methylphenyl | 4-isopropylphenyl |

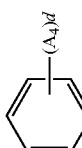

-continued
| | $R_1$ | $R_2$ | $(A_1)a$ | $(A_2)b$ | $(A_3)c$ | $(A_4)d$ |
|---|---|---|---|---|---|---|
| D-72 | tert-Butyl | tert-Butyl |  |  |  |  |
| D-73 | H | Methyl |  |  |  |  |
| D-74 | H | Methyl |  |  |  |  |
| D-75 | H | Methyl |  |  |  |  |
| D-76 | H | Ethyl |  |  |  |  |
| D-77 | H | Ethyl |  |  |  |  |
| D-78 | H | Ethyl |  |  |  |  |

|  | $R_1$ | $R_2$ | $(A_1)a$ | $(A_2)b$ | $(A_3)c$ | $(A_4)d$ |
|---|---|---|---|---|---|---|
| D-79 | H | Isopropyl | Phenyl | 2-Fluorenyl | Phenyl | 2-Fluorenyl |
| D-80 | H | Isopropyl | Phenyl | 4-Methylphenyl | Phenyl | 4-Methylphenyl |
| D-81 | H | Isopropyl | Phenyl | 3-Methylphenyl | Phenyl | 3-Methylphenyl |
| D-82 | Cyclohexyl | Cyclohexyl | 3-Methylphenyl | 3-Methylphenyl | 3-Methylphenyl | 3-Methylphenyl |
| D-83 | Cyclohexyl | Cyclohexyl | 3,5-Dimethylphenyl | 3,5-Dimethylphenyl | 3,5-Dimethylphenyl | 3,5-Dimethylphenyl |
| D-84 | Cyclohexyl | Cyclohexyl | 4-Isopropylphenyl | 4-Isopropylphenyl | 4-Isopropylphenyl | 4-Isopropylphenyl |
| D-85 | Cyclohexyl | Cyclohexyl | 4-Methylphenyl | 4-Methylphenyl | 4-Methylphenyl | 4-Methylphenyl |

| | $R_1$ | $R_2$ | $(A_1)a$ | $(A_2)b$ | $(A_3)c$ | $(A_4)d$ |
|---|---|---|---|---|---|---|
| D-86 | Cyclohexyl | Cyclohexyl | 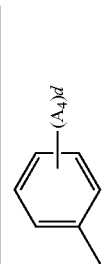 | 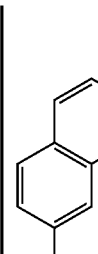 | 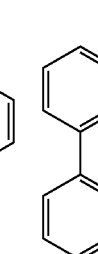 | 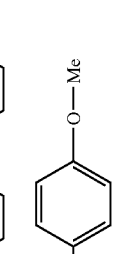 |
| D-87 | Methyl | Methyl | 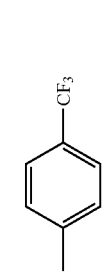 | 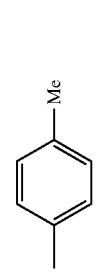 | 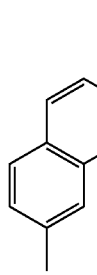 | 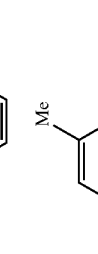 |
| D-88 | Methyl | Methyl | 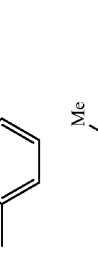 | 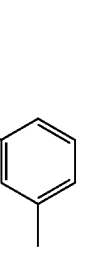 |  |  |
| D-89 | Methyl | Methyl | 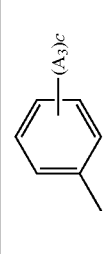 | 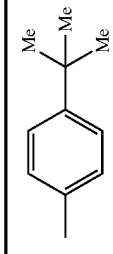 | 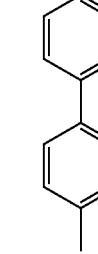 | 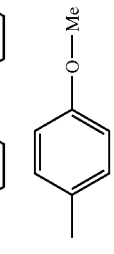 |
| D-90 | Methyl | Methyl | 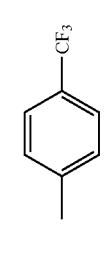 | 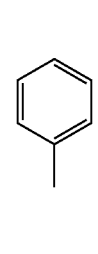 | 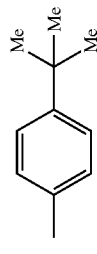 | 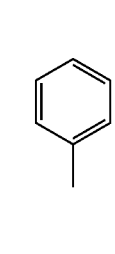 |
| D-91 | Phyenyl | Phyenyl |  | | | |
| D-92 | Phyenyl | Phyenyl | | 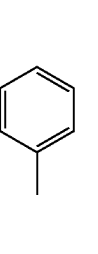 |  | |
| D-93 | Phyenyl | Phyenyl | | | |  |

-continued

| | R$_1$ | R$_2$ | (A$_1$)a | (A$_2$)b | (A$_3$)c | (A$_4$)d |
|---|---|---|---|---|---|---|
| D-94 | Phyenyl | Phyenyl | 3,5-dimethylphenyl | 3,5-dimethylphenyl | 3,5-dimethylphenyl | 3,5-dimethylphenyl |
| D-95 | Phyenyl | Phyenyl | 4-methylphenyl | 4-methylphenyl | 4-methylphenyl | 4-methylphenyl |
| D-96 | Phyenyl | Phyenyl | phenyl | 4-tert-butylphenyl | phenyl | 4-tert-butylphenyl |
| D-97 | Phyenyl | Phyenyl | 2,4-dimethylphenyl | 2,4-dimethylphenyl | 2,4-dimethylphenyl | 2,4-dimethylphenyl |
| D-98 | Phyenyl | Phyenyl | 3-(1-methylethyl)phenyl | 3-(1-methylethyl)phenyl | 3-(1-methylethyl)phenyl | 3-(1-methylethyl)phenyl |
| D-99 | Phyenyl | Phyenyl | phenyl | 5-methylindanyl | phenyl | 5-methylindanyl |
| D-100 | Phyenyl | Phyenyl | phenyl | 6-methyltetrahydronaphthyl | phenyl | 6-methyltetrahydronaphthyl |

-continued
| | $R_1$ | $R_2$ | $(A_1)a$ | $(A_2)b$ | $(A_3)c$ | $(A_4)d$ |
|---|---|---|---|---|---|---|
| D-101 | Phyenyl | Phyenyl | 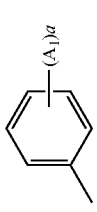 | 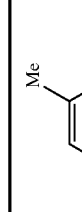 | 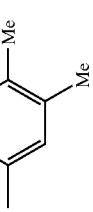 | 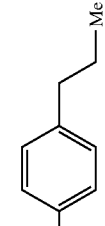 |
| D-102 | Phyenyl | Phyenyl |  |  |  |  |
| D-103 | Phyenyl | Phyenyl | 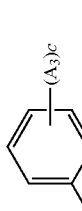 | 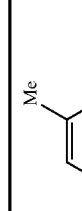 | 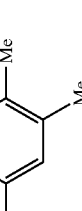 | 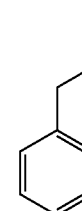 |
| D-104 | Phyenyl | Phyenyl | 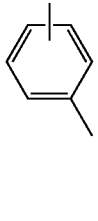 |  | 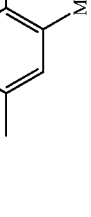 | 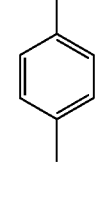 |
| D-105 | Phyenyl | Phyenyl |  |  |  |  |
| D-106 | Phyenyl | Phyenyl |  |  | 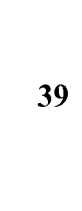 |  |
| D-107 | Phyenyl | Phyenyl | 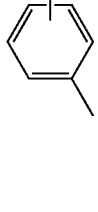 |  | 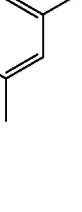 | 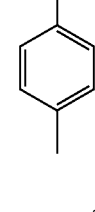 |

-continued

| | $R_1$ | $R_2$ | $(A_1)a$ | $(A_2)b$ | $(A_3)c$ | $(A_4)d$ |
|---|---|---|---|---|---|---|
| D-108 | o-Biphenyl | o-Biphenyl | 4-(2-methylpropan-2-yl)phenyl | 2-methylnaphthyl | 4-(2-methylpropan-2-yl)phenyl | 2-methylnaphthyl |
| D-109 | o-Biphenyl | o-Biphenyl | 3-methylphenyl | 3-methylphenyl | 3-methylphenyl | 3-methylphenyl |
| D-110 | o-Biphenyl | o-Biphenyl | 2,4-dimethylphenyl | 2,4-dimethylphenyl | 2,4-dimethylphenyl | 2,4-dimethylphenyl |
| D-111 | 4-Methylphenyl | 4-Methylphenyl | tetralinyl | tetralinyl | phenyl | tetralinyl |
| D-112 | 4-Methylphenyl | 4-Methylphenyl | 4-methylphenyl | 4-methylphenyl | 4-methylphenyl | 4-methylphenyl |
| D-113 | 4-Methylphenyl | 4-Methylphenyl | 2,3-dimethylphenyl | 2,3-dimethylphenyl | 2,3-dimethylphenyl | 2,3-dimethylphenyl |
| D-114 | 4-Methylphenyl | 4-Methylphenyl | 4-(1,2-dimethylpropyl)phenyl | 4-(naphthalen-2-yl)phenyl | 4-(1,2-dimethylpropyl)phenyl | 4-(naphthalen-2-yl)phenyl |

| | $R_1$ | $R_2$ | $(A_1)a$ | $(A_2)b$ | $(A_3)c$ | $(A_4)d$ |
|---|---|---|---|---|---|---|
| D-115 | 4-Methylphenyl | 4-Methylphenyl | 3,5-Me$_2$-C$_6$H$_3$ | 3,5-Me$_2$-C$_6$H$_3$ | 3,5-Me$_2$-C$_6$H$_3$ | 3,5-Me$_2$-C$_6$H$_3$ |
| D-116 | α,α-Dimethylbenzyl | α,α-Dimethylbenzyl | α,α-dimethyl-4-methylbenzyl | α,α-dimethyl-4-methylphenyl(C) | α,α-dimethyl-4-methylbenzyl | α,α-dimethyl-4-methylphenyl(C) |
| D-117 | α,α-Dimethylbenzyl | α,α-Dimethylbenzyl | phenyl | α,α-dimethyl-4-methylphenyl(C) | phenyl | α,α-dimethyl-4-methylphenyl(C) |
| D-118 | Diphenylamino | Diphenylamino | 4-Me-C$_6$H$_4$ | 4-Me-C$_6$H$_4$ | 4-Me-C$_6$H$_4$ | 4-Me-C$_6$H$_4$ |
| D-119 | Diphenylamino | Diphenylamino | 4-Ph-C$_6$H$_4$ | 4-Ph-C$_6$H$_4$ | 4-Ph-C$_6$H$_4$ | 4-Ph-C$_6$H$_4$ |
| D-120 | Cyano | Cyano | 4-CN-C$_6$H$_4$ | 4-CN-C$_6$H$_4$ | 4-CN-C$_6$H$_4$ | 4-CN-C$_6$H$_4$ |
| D-121 | Cyano | Cyano | 4-CF$_3$-C$_6$H$_4$ | 4-CF$_3$-C$_6$H$_4$ | 4-CF$_3$-C$_6$H$_4$ | 4-CF$_3$-C$_6$H$_4$ |
| D-122 | 4-Benzonitrile | 4-Benzonitrile | 2,4-Me$_2$-C$_6$H$_3$ | 2,4-Me$_2$-C$_6$H$_3$ | 2,4-Me$_2$-C$_6$H$_3$ | 2,4-Me$_2$-C$_6$H$_3$ |

| | $R_1$ | $R_2$ | 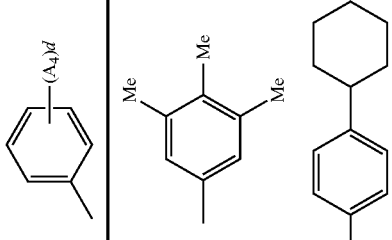 (A₁)a | 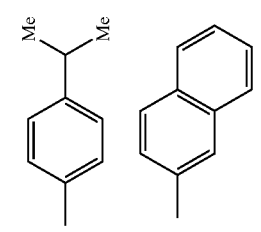 (A₂)b | 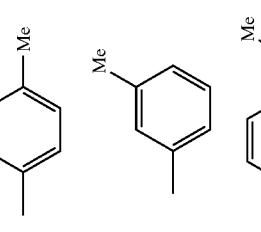 (A₃)c | 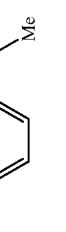 (A₄)d |
|---|---|---|---|---|---|---|
| D-123 | 4-Benzonitrile | 4-Benzonitrile | 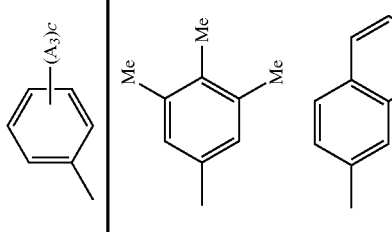 | 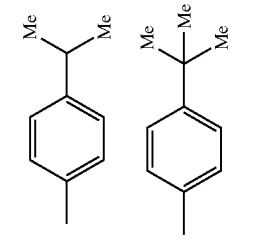 | 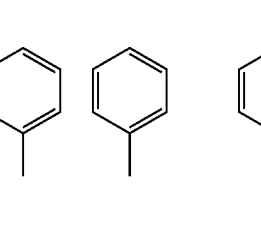 | 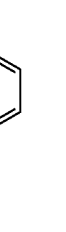 |
| D-124 | 2-Phenylethyl | 2-Phenylethyl | 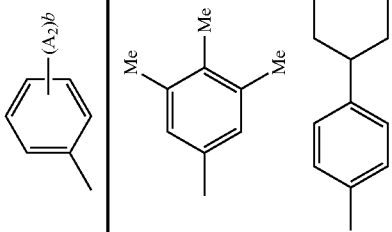 | 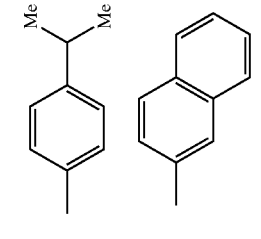 | 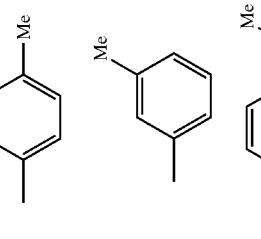 | 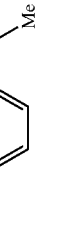 |
| D-125 | 2-Phenylethyl | 2-Phenylethyl | 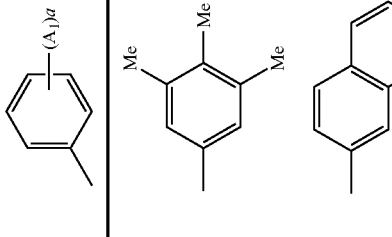 | 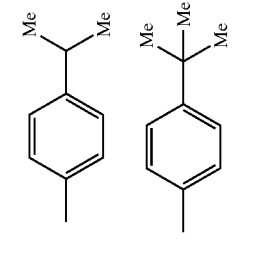 | 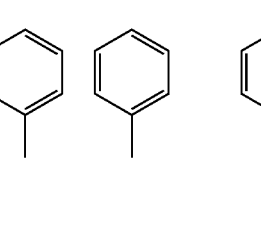 | 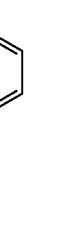 |
| D-126 | 3,5-Dimethylphenyl | 3,5-Dimethylphenyl | 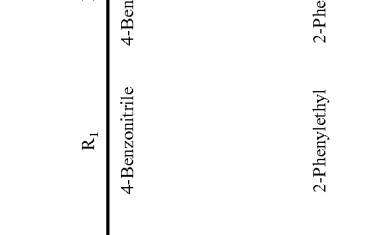 | 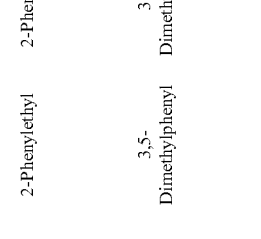 | 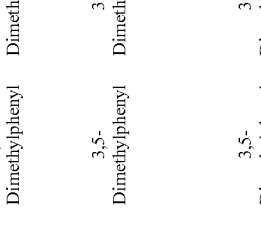 |  |
| D-127 | 3,5-Dimethylphenyl | 3,5-Dimethylphenyl |  |  |  |  |
| D-128 | 3,5-Dimethylphenyl | 3,5-Dimethylphenyl | | | | |
| D-129 | 3,5-Dimethylphenyl | 3,5-Dimethylphenyl | | | | |

-continued

| | R₁ | R₂ | (A₁)a | (A₂)b | (A₃)c | (A₄)d |
|---|---|---|---|---|---|---|
| D-130 | 3,5-Dimethylphenyl | 3,5-Dimethylphenyl | 3-methylphenyl | 3-methylphenyl | 3-methylphenyl | 3-methylphenyl |
| D-131 | 3,5-Dimethylphenyl | 3,5-Dimethylphenyl | 2,6-dimethylphenyl | 2,6-dimethylphenyl | 2,6-dimethylphenyl | 2,6-dimethylphenyl |
| D-132 | 3,5-Dimethylphenyl | 3,5-Dimethylphenyl | 4-methylphenyl | 4-methylphenyl | 4-methylphenyl | 4-methylphenyl |
| D-133 | 3,5-Dimethylphenyl | 3,5-Dimethylphenyl | 4-isopropylphenyl | 3,5-dimethylphenyl | 4-isopropylphenyl | 3,5-dimethylphenyl |
| D-134 | 3,5-Dimethylphenyl | 3,5-Dimethylphenyl | 4-ethylphenyl(Me,Me) | 4-ethylphenyl | 4-ethylphenyl | 4-ethylphenyl(Me,Me) |
| D-135 | 3,5-Dimethylphenyl | 3,5-Dimethylphenyl | 4-tert-butylphenyl | 4-ethylphenyl | 4-tert-butylphenyl | 4-ethylphenyl |
| D-136 | 3,5-Dimethylphenyl | 3,5-Dimethylphenyl | 2,4-dimethylphenyl | 2,4-dimethylphenyl | 2,4-dimethylphenyl | 2,4-dimethylphenyl |

-continued

| | $R_1$ | $R_2$ | $(A_1)a$ | $(A_2)b$ | $(A_3)c$ | $(A_4)d$ |
|---|---|---|---|---|---|---|
| D-137 | 3,5-Dimethylphenyl | 3,5-Dimethylphenyl | 4-methylphenyl | 4-(1-methylethyl)phenyl with Me groups | 4-methylphenyl | 4-(1-methylethyl)phenyl with Me groups |
| D-138 | 3,5-Dimethylphenyl | 3,5-Dimethylphenyl | 3,5-dimethylphenyl | 3,5-dimethylphenyl | 3,5-dimethylphenyl | 3,5-dimethylphenyl |
| D-139 | 3,5-Dimethylphenyl | 3,5-Dimethylphenyl | 4-(1-methylethyl)phenyl with Me groups | 4-cyclohexylphenyl | 4-(1-methylethyl)phenyl with Me groups | 4-cyclohexylphenyl |
| D-140 | 3,5-Dimethylphenyl | 3,5-Dimethylphenyl | 4-methylphenyl | 4-phenylphenyl | 4-methylphenyl | 4-phenylphenyl |
| D-141 | 3,5-Dimethylphenyl | 3,5-Dimethylphenyl | 4-methylphenyl | 4-methylphenyl | 4-methylphenyl | 4-methylphenyl |
| D-142 | 3,5-Dimethylphenyl | 3,5-Dimethylphenyl | 6-methylnaphthyl | 6-methylnaphthyl | 6-methylnaphthyl | 6-methylnaphthyl |
| D-143 | 1-Naphthyl | 1-Naphthyl | 4-(1,1-dimethylethyl)phenyl with Me groups | 6-methylnaphthyl | 4-(1,1-dimethylethyl)phenyl with Me groups | 6-methylnaphthyl |

-continued

| | $R_1$ | $R_2$ | $(A_1)a$ | $(A_2)b$ | $(A_3)c$ | $(A_4)d$ |
|---|---|---|---|---|---|---|
| D-144 | 1-Naphthyl | 1-Naphthyl | Phenyl | 3-Me-phenyl | Phenyl | 3-Me-phenyl |
| D-145 | 1-Naphthyl | 1-Naphthyl | 3-Me-phenyl | 3-Me-phenyl | 3-Me-phenyl | 3-Me-phenyl |
| D-146 | 1-Naphthyl | 1-Naphthyl | Phenyl | 4-Me-phenyl | Phenyl | 4-Me-phenyl |
| D-147 | 1-Naphthyl | 1-Naphthyl | 2,4-diMe-phenyl | 2,4-diMe-phenyl | 2,4-diMe-phenyl | 2,4-diMe-phenyl |
| D-148 | 1-Naphthyl | 1-Naphthyl | 2,6-diMe-phenyl | 2,6-diMe-phenyl | 2,6-diMe-phenyl | 2,6-diMe-phenyl |
| D-149 | 1-Naphthyl | 1-Naphthyl | 4-Me-phenyl | 4-Me-phenyl | 4-Me-phenyl | 4-Me-phenyl |
| D-150 | 1-Naphthyl | 1-Naphthyl | 4-iPr-phenyl | 3,5-diMe-phenyl | 4-iPr-phenyl | 3,5-diMe-phenyl |

-continued

| | R₁ | R₂ | (A₁)a | (A₂)b | (A₃)c | (A₄)d |
|---|---|---|---|---|---|---|
| D-151 | 1-Naphthyl | 1-Naphthyl | 4-(1-methylethyl)phenyl | 4-(1-methylethyl)phenyl | 4-(1-methylethyl)phenyl | 4-(1-methylethyl)phenyl |
| D-152 | 1-Naphthyl | 1-Naphthyl | 4-tert-butylphenyl | 4-tert-butylphenyl | 4-tert-butylphenyl | 4-tert-butylphenyl |
| D-153 | 1-Naphthyl | 1-Naphthyl | phenyl | 4-(1-methylethyl)phenyl | phenyl | 4-(1-methylethyl)phenyl |
| D-154 | 1-Naphthyl | 1-Naphthyl | 4-methylphenyl | 4-(1-methylethyl)phenyl | 4-methylphenyl | 4-(1-methylethyl)phenyl |
| D-155 | 1-Naphthyl | 1-Naphthyl | 4-(1-methylethyl)phenyl | cyclohexylphenyl | 4-(1-methylethyl)phenyl | cyclohexylphenyl |
| D-156 | 1-Naphthyl | 1-Naphthyl | 3,5-dimethylphenyl | 3,5-dimethylphenyl | 3,5-dimethylphenyl | 3,5-dimethylphenyl |
| D-157 | 1-Naphthyl | 1-Naphthyl | phenyl | biphenyl | phenyl | biphenyl |
| D-158 | 1-Naphthyl | 1-Naphthyl | phenyl | 2-naphthyl | phenyl | 2-naphthyl |

-continued

| | $R_1$ | $R_2$ | $(A_1)a$ | $(A_2)b$ | $(A_3)c$ | $(A_4)d$ |
|---|---|---|---|---|---|---|
| D-159 | 1-Naphthyl | 1-Naphthyl | 2-Naphthyl | 2-Naphthyl | 2-Naphthyl | 2-Naphthyl |
| D-160 | 2-Naphthyl | 2-Naphthyl | 4-(tert-butyl)phenyl | 2-Naphthyl | 4-(tert-butyl)phenyl | 2-Naphthyl |
| D-161 | 2-Naphthyl | 2-Naphthyl | Phenyl | 4-Methylphenyl | Phenyl | 4-Methylphenyl |
| D-162 | 2-Naphthyl | 2-Naphthyl | Phenyl | 3-Methylphenyl | Phenyl | 3-Methylphenyl |
| D-163 | 2-Naphthyl | 2-Naphthyl | Phenyl | 4-(isopropyl)phenyl | Phenyl | 4-(isopropyl)phenyl |
| D-164 | 2-Naphthyl | 2-Naphthyl | 3-Methylphenyl | 3-Methylphenyl | 3-Methylphenyl | 3-Methylphenyl |
| D-165 | 2-Naphthyl | 2-Naphthyl | 3,5-Dimethylphenyl | 3,5-Dimethylphenyl | 3,5-Dimethylphenyl | 3,5-Dimethylphenyl |

-continued

| | $R_1$ | $R_2$ | $(A_1)a$ | $(A_2)b$ | $(A_3)c$ | $(A_4)d$ |
|---|---|---|---|---|---|---|
| D-166 | 2-Naphthyl | 2-Naphthyl | 4-MeC6H4 | 4-MeC6H4 | 4-MeC6H4 | 4-MeC6H4 |
| D-167 | 2-Naphthyl | 2-Naphthyl | 4-(CHMe2)C6H4 | 3,5-Me2C6H3 | 4-(CHMe2)C6H4 | 3,5-Me2C6H3 |
| D-168 | 2-Naphthyl | 2-Naphthyl | 4-(CHMe2)C6H4 | 4-(CHMe2)C6H4 | 4-(CHMe2)C6H4 | 4-(CHMe2)C6H4 |
| D-169 | 2-Naphthyl | 2-Naphthyl | 4-(CMe3)C6H4 | 4-(CMe3)C6H4 | 4-(CMe3)C6H4 | 4-(CMe3)C6H4 |
| D-170 | 2-Naphthyl | 2-Naphthyl | 2,4-Me2C6H3 | 2,4-Me2C6H3 | 2,4-Me2C6H3 | 2,4-Me2C6H3 |
| D-171 | 2-Naphthyl | 2-Naphthyl | 4-MeC6H4 | 4-(CHMe2)C6H4 | 4-MeC6H4 | 4-(CHMe2)C6H4 |
| D-172 | 2-Naphthyl | 2-Naphthyl | 3,5-Me2C6H3 | 3,5-Me2C6H3 | 3,5-Me2C6H3 | 3,5-Me2C6H3 |

-continued

| | $R_1$ | $R_2$ | $(A_1)a$ | $(A_2)b$ | $(A_3)c$ | $(A_4)d$ |
|---|---|---|---|---|---|---|
| D-173 | 2-Naphthyl | 2-Naphthyl | 4-(isopropyl)phenyl | 4-cyclohexylphenyl | 4-(isopropyl)phenyl | 4-cyclohexylphenyl |
| D-174 | 2-Naphthyl | 2-Naphthyl | 4-methylphenyl | 4-methylbiphenyl | 4-methylphenyl | 4-methylbiphenyl |
| D-175 | 2-Naphthyl | 2-Naphthyl | 4-methylphenyl | 6-methyl-2-naphthyl | 4-methylphenyl | 6-methyl-2-naphthyl |
| D-176 | 2-Naphthyl | 2-Naphthyl | 6-methyl-2-naphthyl | 6-methyl-2-naphthyl | 6-methyl-2-naphthyl | 6-methyl-2-naphthyl |

In the aromatic amine derivative represented by any one of the general formulae (1) to (7) of the present invention, a diaminonaphthalene structure as a light emitting center is coupled with a benzene ring having a substituent. As a result, the molecules of the compound are prevented from associating with each other, and hence the lifetime of an organic EL device using the compound is prolonged. In addition, a bulky substituent is introduced into a naphthalene skeleton at a position (3 or 7-position) distant from the position at which an amino group is bonded (1 or 5-position), whereby the molecules of the compound are prevented from associating with each other without the occurrence of steric repulsion in an amino group-naphthalene bond, and hence the lifetime of the organic EL device using the compound is additionally prolonged.

In addition, the derivative is strongly fluorescent in a solid state, is excellent in electroluminescent property, and has a fluorescent quantum efficiency of 0.3 or more. Further, the derivative brings together excellent properties with which a hole is injected and transported from a metal electrode or an organic thin film layer, and excellent properties with which an electron is injected and transported from the metal electrode or the organic thin film layer, whereby the derivative is effectively used as a light emitting material for an organic EL device, in particular, a doping material for an organic EL device. Further, any other hole transporting material, electron transporting material, or doping material may be used.

An organic EL device of the present invention is a device having an organic thin film layer composed of one or more layers and formed between an anode and a cathode. When the organic thin film layer is composed of one layer, alight emitting layer is provided between the anode and the cathode. The light emitting layer contains a light emitting material, and may contain a hole injecting material or an electron injecting material in addition to the light emitting material in order that a hole injected from the anode or an electron injected from the cathode may be transported to the light emitting material. The aromatic amine derivative represented by any one of the general formulae (1) to (7) can be used in the organic thin film layer because the derivative has high light emitting property, and has excellent hole injecting property, excellent hole transporting property, excellent electron injecting property, and excellent electron transporting property; the derivative is preferably used as the light emitting material in the light emitting layer.

In the organic EL device of the present invention, the light emitting layer contains the aromatic amine derivative of the present invention at a content of preferably 0.1 to 20 wt %, or more preferably 1 to 10 wt %. In addition, the light emitting layer can be formed only of the aromatic amine derivative represented by any one of the general formulae (1) to (7) of the present invention because the aromatic amine derivative brings together extremely high fluorescent quantum efficiency, a high hole transporting ability, and a high electron transporting ability, and can be formed into a uniform thin film.

In addition, the organic EL device of the present invention is preferably an organic EL device having an organic thin film layer composed of two or more layers including at least a light emitting layer and interposed between a cathode and an anode, in which an organic layer mainly composed of the aromatic amine derivative represented by any one of the general formulae (1) to (7) is present between the anode and the light emitting layer. Examples of the organic layer include a hole injecting layer and a hole transporting layer.

The organic EL device having multiple layers is a laminate having, for example, an (anode/hole injecting layer/light emitting layer/cathode), (anode/light emitting layer/electron injecting layer/cathode), or (anode/hole injecting layer/light emitting layer/electron injecting layer/cathode) multiple layer constitution.

Further, when the organic EL device contains the aromatic amine derivative of the present invention as a doping material, the device preferably contains at least one kind selected from an anthracene derivative represented by the following general formula (8), an anthracene derivative represented by the following general formula (9), and a pyrene derivative represented by the following general formula (10) as a host material:

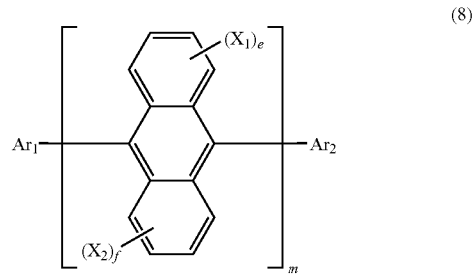

(8)

in the general formula (8):

$X_1$ and $X_2$ each independently represent a hydrogen atom, a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted alkoxyl group having 1 to 50 carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted heterocyclic group having 5 to 50 ring carbon atoms, or a halogen atom, e and f each independently represent an integer of 0 to 4, and when e or f represents 2 or more, $X_1$s or $X_2$s may be identical to or different from each other;

$Ar_1$ and $Ar_2$ each independently represent a substituted or unsubstituted aryl group having 5 to 50 ring carbon atoms, or a substituted or unsubstituted heterocyclic group having 5 to 50 ring carbon atoms, and at least one of $Ar_1$ and $Ar_2$ represents a substituted or unsubstituted, fused ring-containing aryl group having 10 to 50 ring carbon atoms; and m represents an integer of 1 to 3, and when m represents 2 or more, groups in [ ] may be identical to or different from each other.

Specific examples of each group represented by any one of $X_1$ and $X_2$, and $Ar_1$ and $Ar_2$, and specific examples of a substituent for the group include examples similar to those described for the general formula (1):

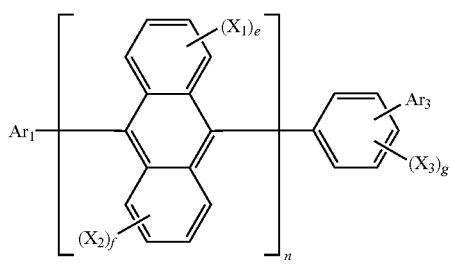

in the general formula (9):

$X_1$ to $X_3$ each independently represent a hydrogen atom, a substituted or unsubstituted alkyl group having 1 to 50 carbon atoms, a substituted or unsubstituted aryl group having 5 to 50 ring carbon atoms, a substituted or unsubstituted aralkyl group having 6 to 50 ring carbon atoms, a substituted or unsubstituted cycloalkyl group having 3 to 50 ring carbon atoms, a substituted or unsubstituted alkoxyl group having 1 to 50 carbon atoms, a substituted or unsubstituted aryloxy group having 5 to 50 ring carbon atoms, a substituted or unsubstituted arylamino group having 5 to 50 ring carbon atoms, a substituted or unsubstituted alkylamino group having 1 to 20 carbon atoms, a substituted or unsubstituted heterocyclic group having 5 to 50 ring carbon atoms, or a halogen atom, e, f, and g each independently represent an integer of 0 to 4, and when e, f, or g represents 2 or more, $X_1$s, $X_2$s, or $X_3$s may be identical to or different from each other;

$Ar_1$ represents a substituted or unsubstituted, fused ring-containing aryl group having 10 to 50 ring carbon atoms, and $Ar_3$ represents a substituted or unsubstituted aryl group having 5 to 50 ring carbon atoms; and n represents an integer of 1 to 3, and when n represents 2 or more, groups in [ ] may be identical to or different from each other.)

Specific examples of each group represented by any one of $X_1$ to $X_3$, and $Ar_1$ to $Ar_3$, and specific examples of a substituent for the group include examples similar to those described for the general formula (1).

Specific examples of the anthracene derivative represented by each of the general formulae (8) and (9) are shown below. However, the present invention is not limited to these exemplified compounds:

AN1

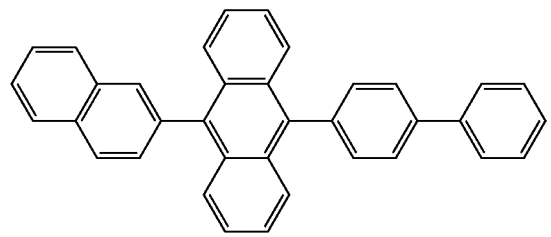

AN2

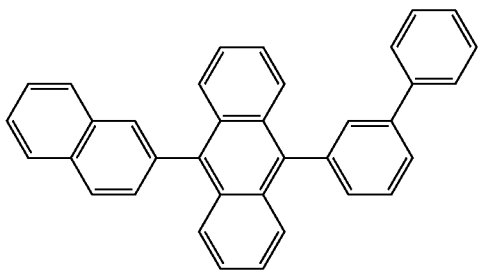

AN3

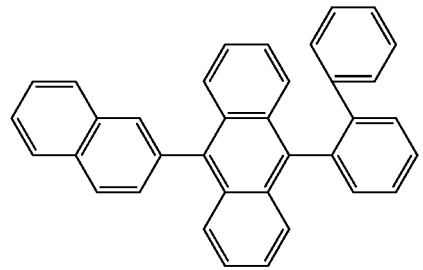

AN4

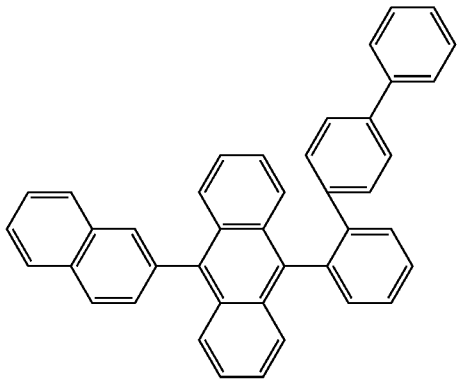

AN5

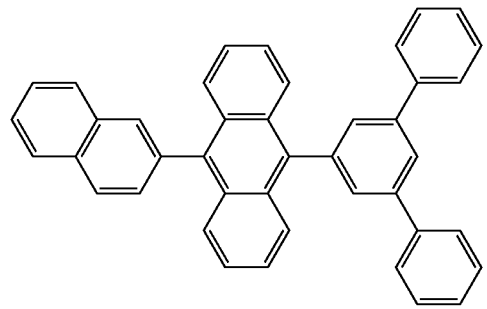

AN6

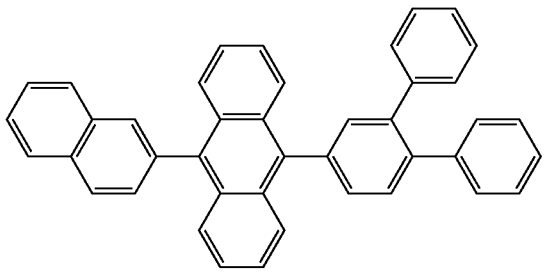

-continued
AN7
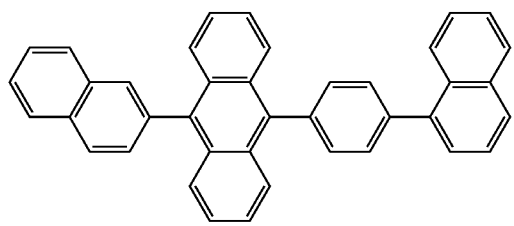
AN8
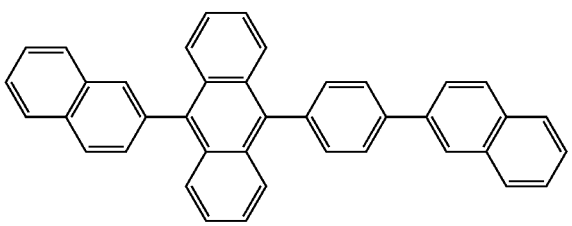
AN9
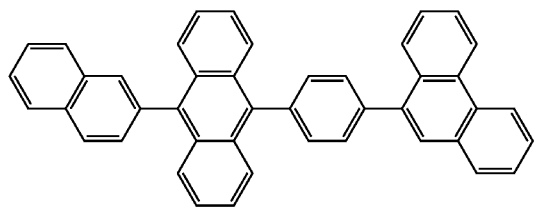
AN10
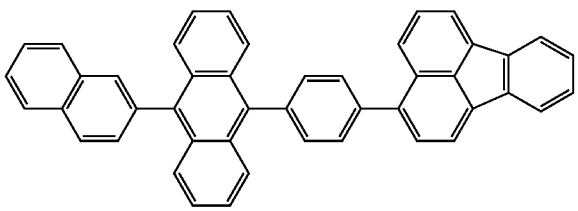
AN11
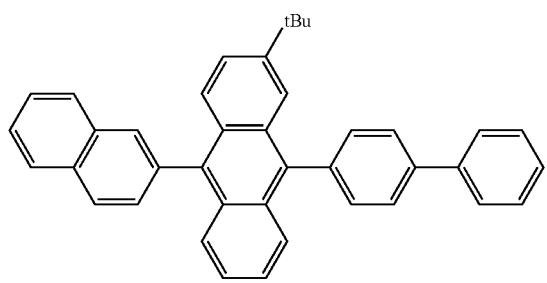
AN12
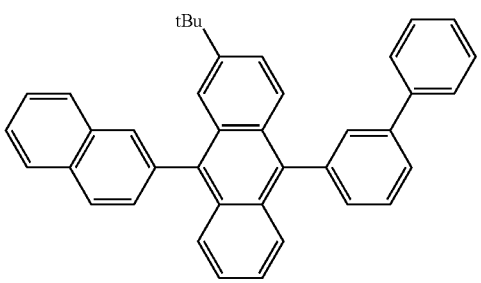
AN13
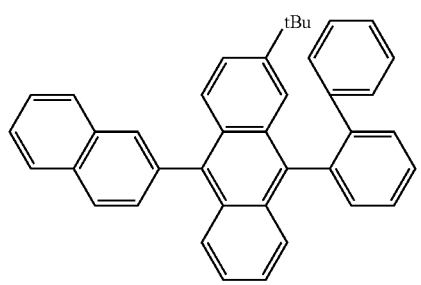
AN14
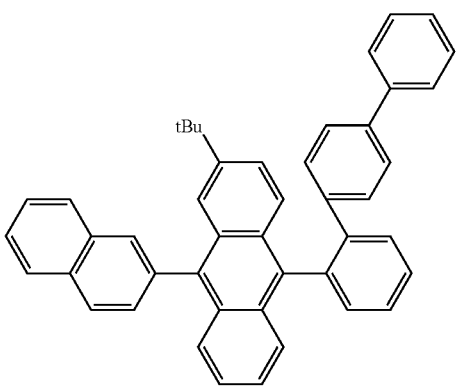
AN15
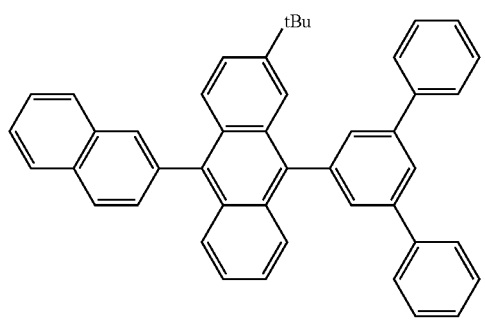
AN16
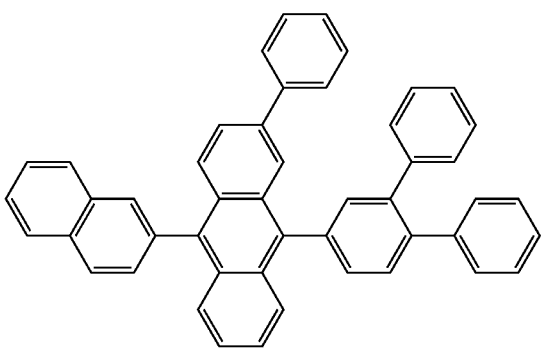

-continued
AN17
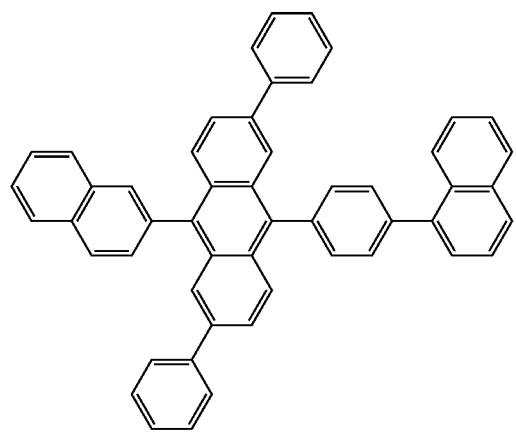
AN18
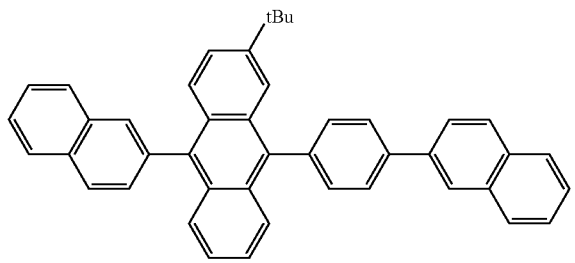
AN19
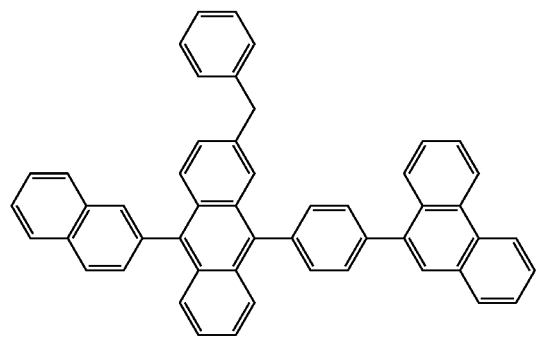
AN20
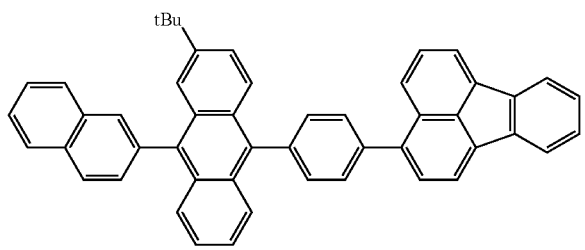
AN21
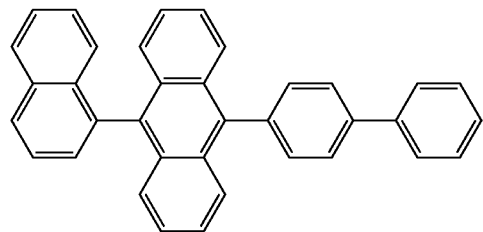
AN22
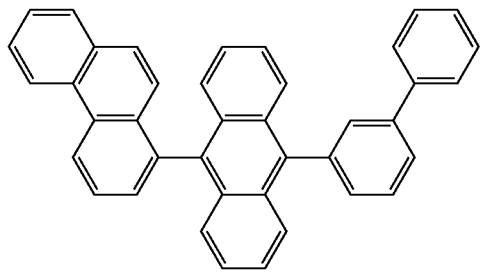
AN23
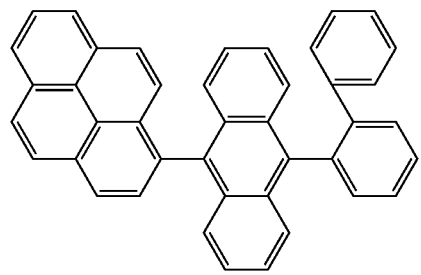
AN24
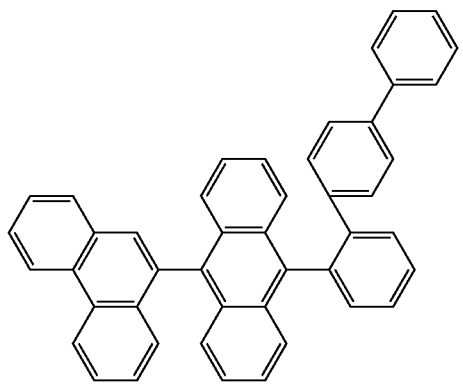

-continued
AN25
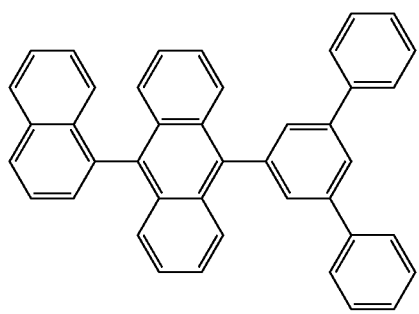
AN26
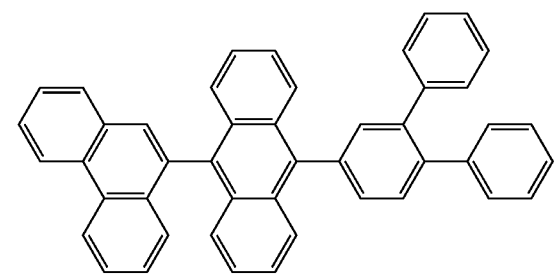
AN27
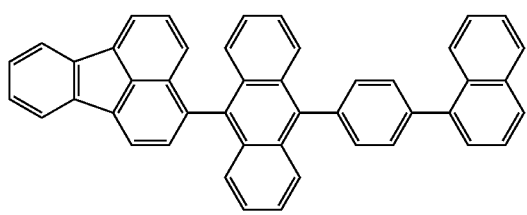
AN28
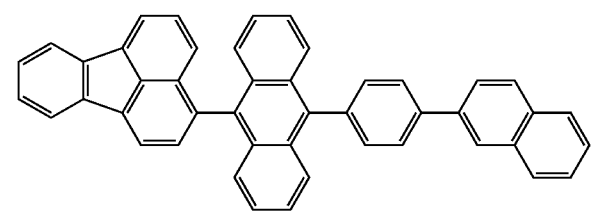
AN29
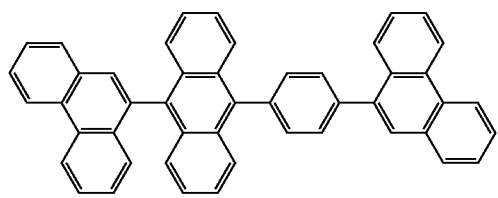
AN30
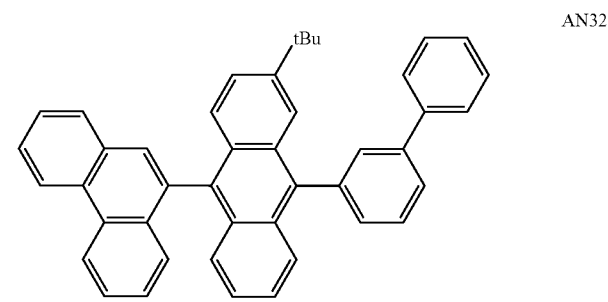
AN31
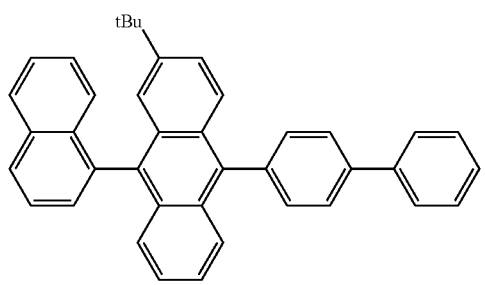
AN32
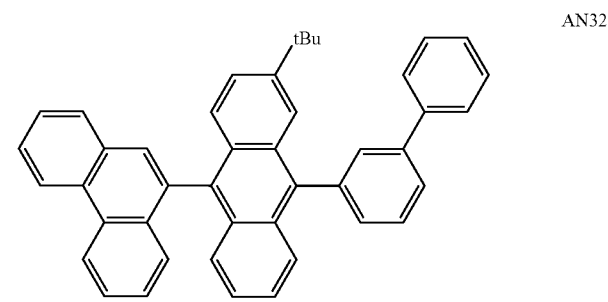
AN33
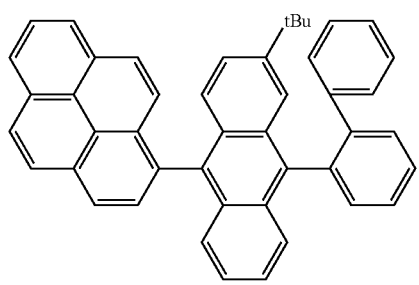
AN34
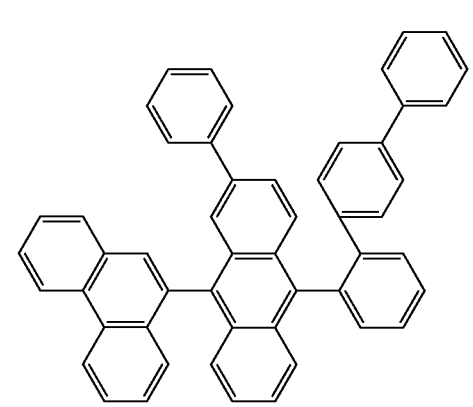

-continued
AN35
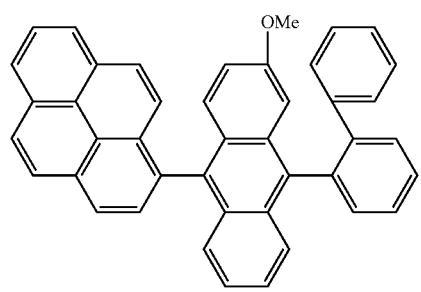
AN36
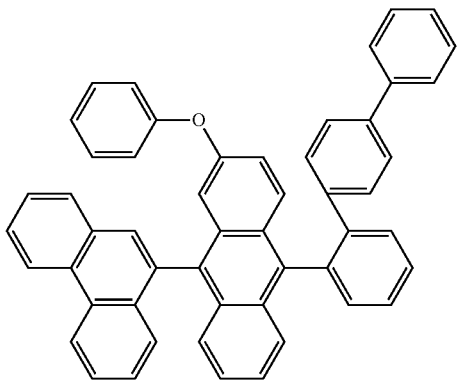
AN37
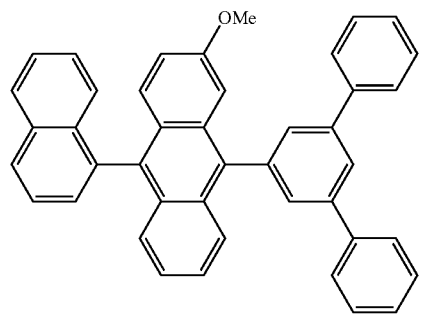
AN38
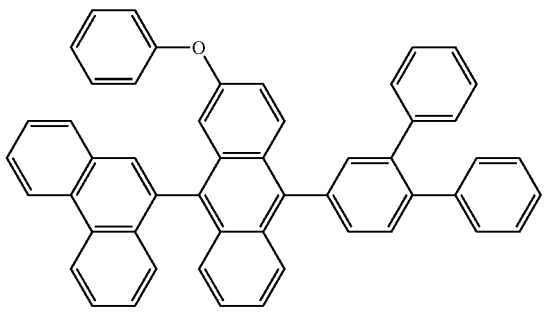
AN39
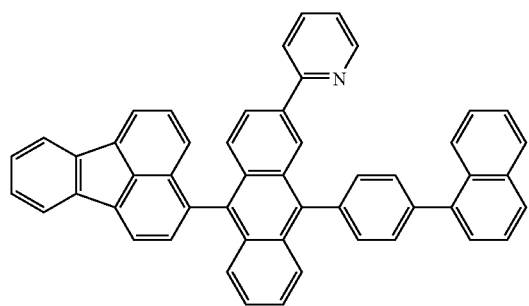
AN40
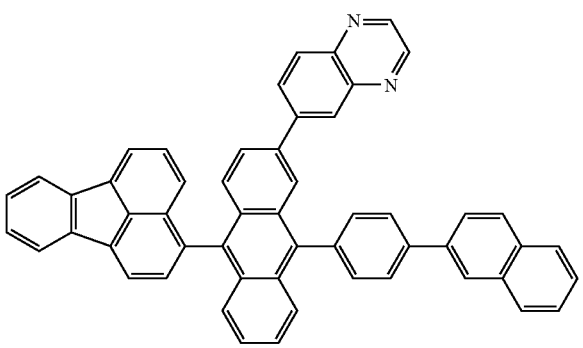
AN41
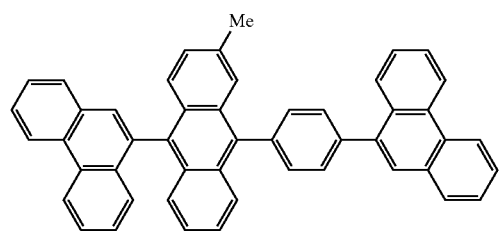
AN42
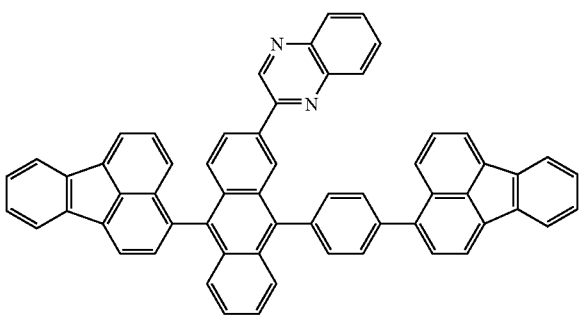

-continued

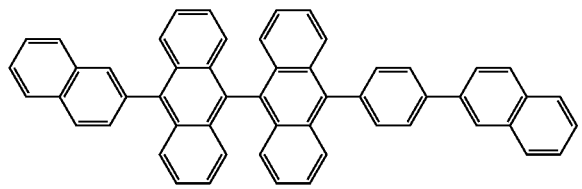
AN43

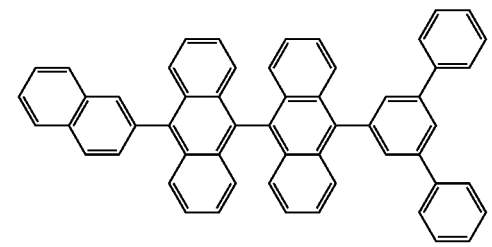
AN44

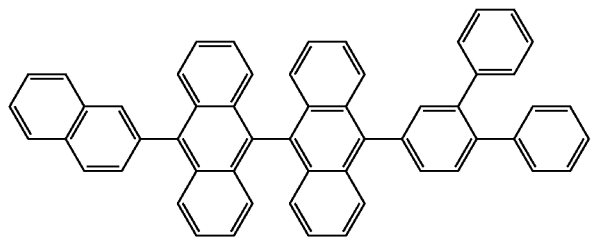
AN45

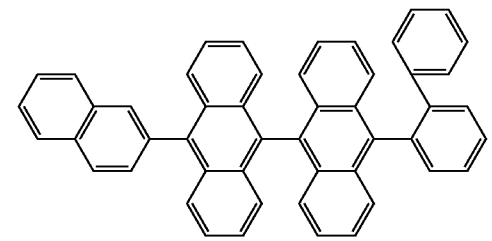
AN46

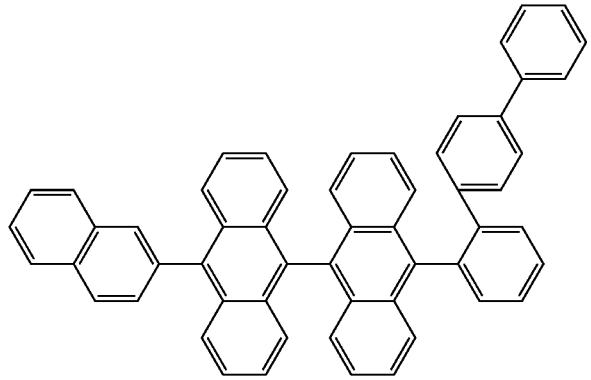
AN47

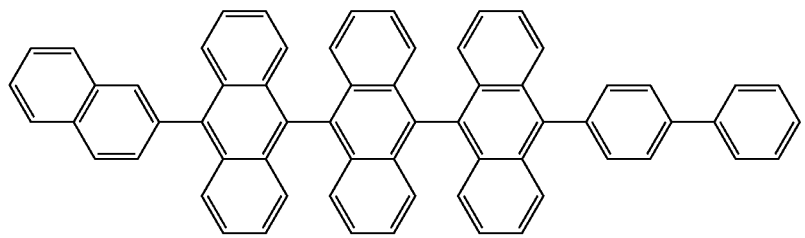
AN48

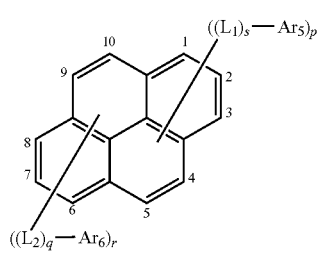

(10)

in the general formula (10):

$Ar_5$ and $Ar_6$ each independently represent a substituted or unsubstituted aryl group having 6 to 50 ring carbon atoms;

$L_1$ and $L_2$ each independently represent a substituted or unsubstituted phenylene group, a substituted or unsubstituted naphthalenylene group, a substituted or unsubstituted fluorenylene group, or a substituted or unsubstituted dibenzosilolylene group;

s represents an integer of 0 to 2, p represents an integer of 1 to 4, q represents an integer of 0 to 2, and r represents an integer of 0 to 4; and $L_1$ or $Ar_5$ is bonded to any one of 1- to 5-positions of pyrene, and $L_2$ or $Ar_6$ is bonded to any one of 6- to 10-positions of pyrene, provided that, when p+r represents an even number, $Ar_5$, $Ar_6$, $L_1$, and $L_2$ satisfy the following relationship (1) or (2):

(1) $Ar_5 \neq Ar_6$ and/or $L_1 \neq L_2$ (where ≠ means that groups on both sides of the symbol are different from each other in structure); or (2) for $Ar_5 = Ar_6$ and $L_1 = L_2$,
 (2-1) when $s \neq q$ and/or $p \neq r$, or
 (2-2) when $s = q$ and $p = r$,
  (2-2-1) in the case where $L_1$ and $L_2$ are, or pyrene is, bonded to different bonding positions on $Ar_5$ and $Ar_6$, or
  (2-2-2) in the case where $L_1$ and $L_2$ are, or pyrene is, bonded to the same bonding position on $Ar_5$ and $Ar_6$,
 the case where the substitution positions of $L_1$ and $L_2$ or of $Ar_5$ and $Ar_6$ in pyrene are 1- and 6-positions or 2- and 7-positions is excluded.

Specific examples of each group represented by any one of $Ar_5$ and $Ar_6$, and $L_1$ and $L_2$, and specific examples of a substituent for the group include examples similar to those described for the general formula (1).

Specific examples of the pyrene derivative represented by the general formulae (5) are shown below. However, the present invention is not limited to these exemplified compounds.

P1

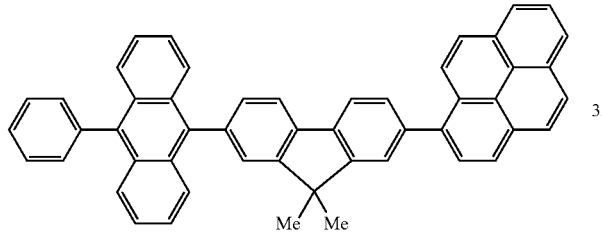

P2

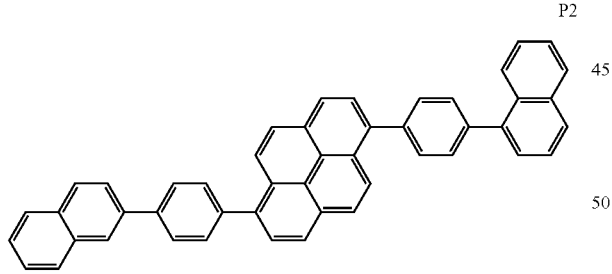

P3

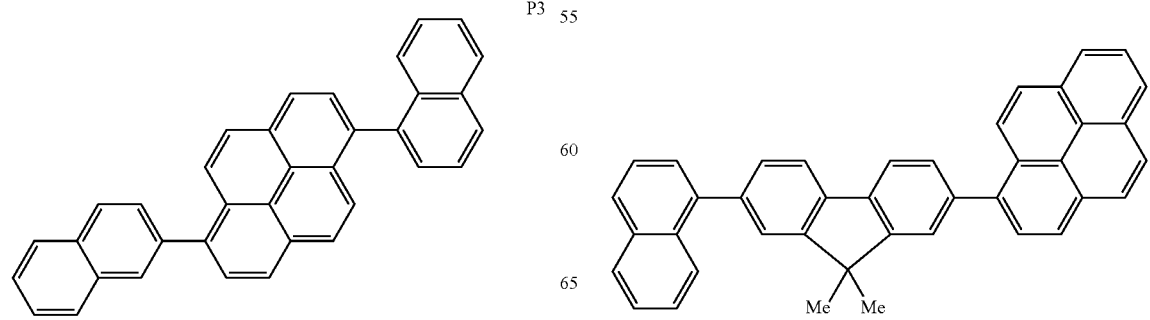

P4

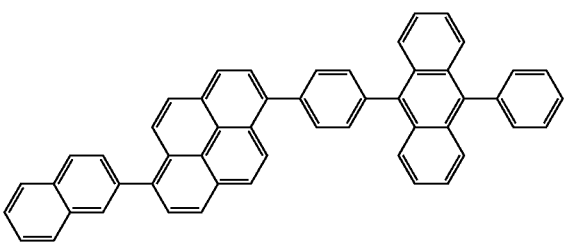

P5

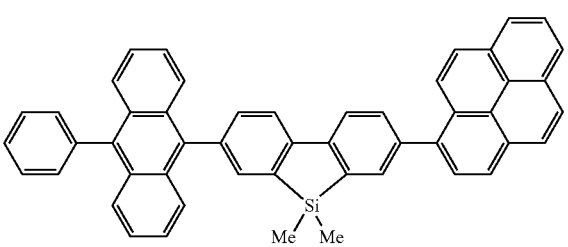

P6

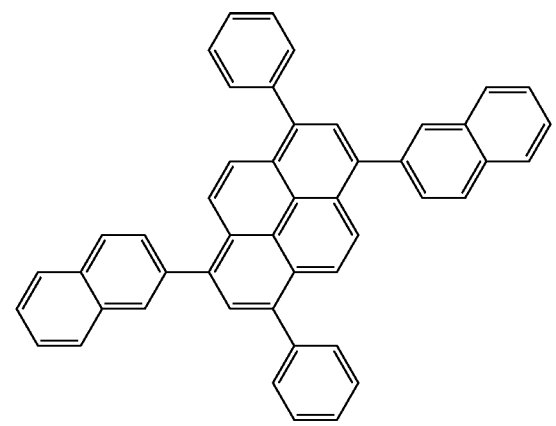

P7

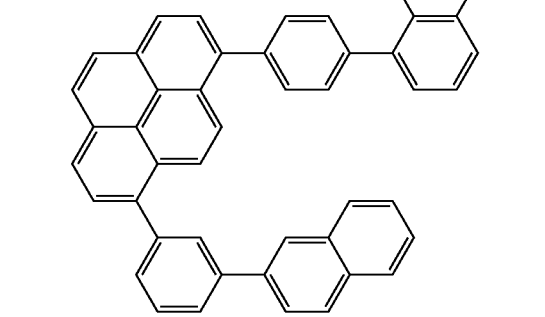

P8

-continued
P9
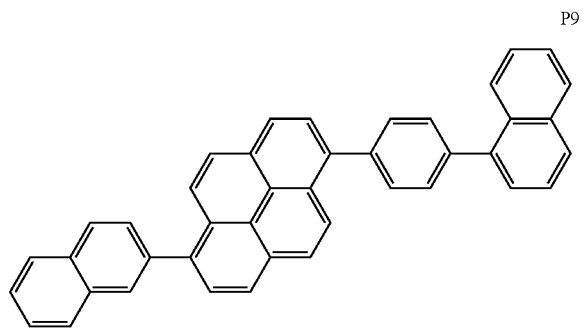
P10
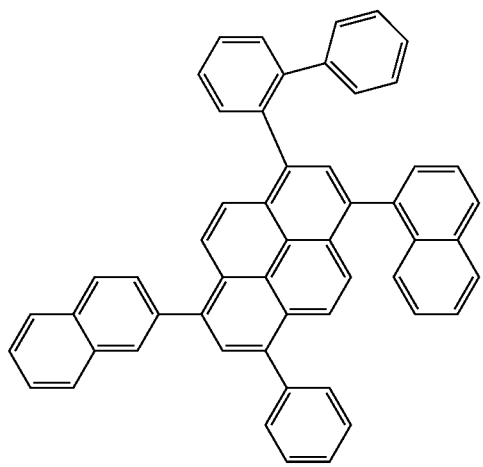
P11
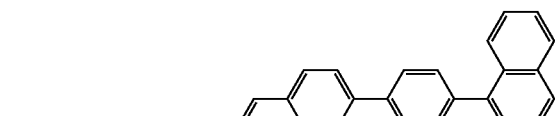
P12
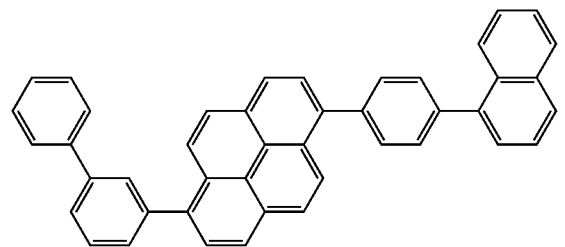
-continued
P13
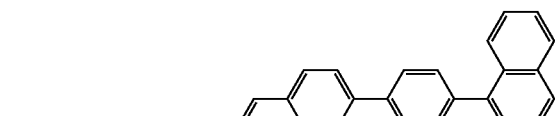
P14
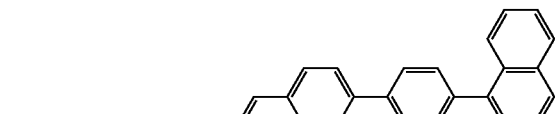
P15
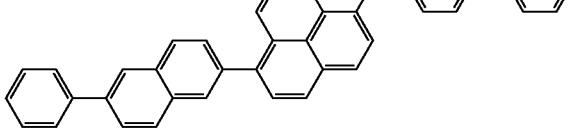
P16
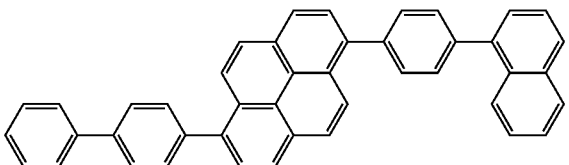
P17
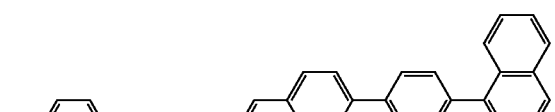
P18
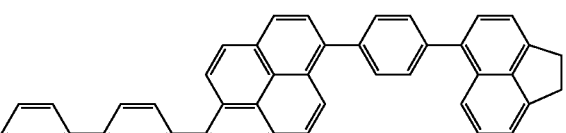

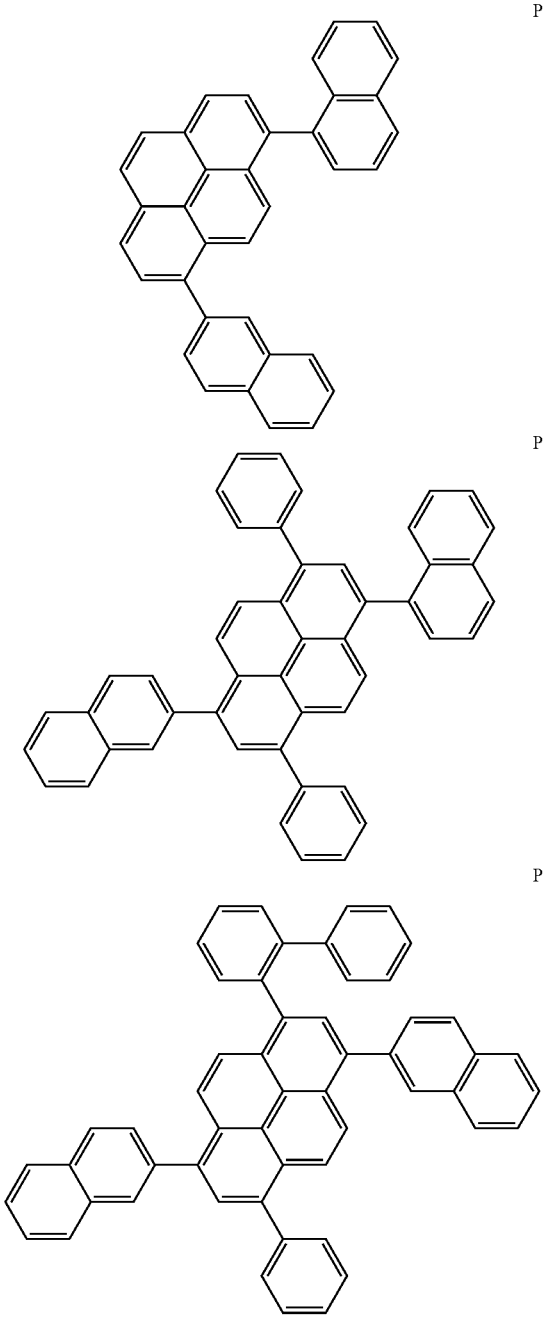

In the present invention, the organic EL device having multiple organic thin film layers is a laminate having, for example, an (anode/hole injecting layer/light emitting layer/cathode), (anode/light emitting layer/electron injecting layer/cathode), or (anode/hole injecting layer/light emitting layer/electron injecting layer/cathode) constitution.

In addition to the aromatic amine derivative of the present invention, an additional known light emitting material, doping material, hole injecting material, or electron injecting material can be used as required in the multiple layers. When the organic EL device has the multiple organic thin film layers, a reduction in luminance or lifetime due to quenching can be prevented. If needed, a light emitting material, a doping material, a hole injecting material, and an electron injecting material can be used in combination. In addition, a doping material can provide improvements in emission luminance and luminous efficiency, and red or blue light emission. In addition, each of the hole injecting layer, the light emitting layer, and the electron injecting layer may be formed of a layer constitution having two or more layers. At that time, in the case of the hole injecting layer, a layer for injecting a hole from the electrode is referred to as a hole injecting layer, and a layer for receiving the hole from the hole injecting layer and transporting the hole to the light emitting layer is referred to as a hole transporting layer. In the same manner, in the case of the electron injecting layer, a layer for injecting an electron from the electrode is referred to as an electron injecting layer, and a layer for receiving the electron from the electron injecting layer and transporting the electron to the light emitting layer is referred to as an electron transporting layer. Each of those layers is selected and used depending on factors such as the energy level of a material, heat resistance, and adhesiveness between the layer and an organic layer or a metal electrode.

Examples of a host material or a doping material other than those in the above general formulae (3) to (5) which can be used in the light emitting layer together with the aromatic amine derivative of the present invention include, but are not limited to: fused polycyclic aromatic compounds such as naphthalene, phenanthrene, rubrene, anthracene, tetracene, pyrene, perylene, chrysene, decacyclene, coronene, tetraphenylcyclopentadiene, pentaphenylcyclopentadiene, fluorene, spirofluorene, 9,10-diphenylanthracene, 9,10-bis(phenylethynyl)anthracene, and 1,4-bis(9'-ethynylanthracene)benzene and derivatives thereof; organic metal complexes such as tris(8-quinolinolato)aluminum and bis-(2-methyl-8-quinolinolato)-4-(phenylphenolinato)aluminum; a triarylamine derivative; a styrylamine derivative; a stilbene derivative; a coumarin derivative; a pyrane derivative; an oxazone derivative; a benzothiazole derivative; a benzoxazole derivative; a benzoimidazole derivative; a pyrazine derivative; a cinnamate derivative; a diketopyrrolopyrrole derivative; an acridone derivative; and quinacridone derivative.

A compound having an ability of transporting a hole, having hole injection efficiency from an anode and excellent hole injection efficiency to a light emitting layer or a light emitting material, preventing the migration of an exciton generated in the light emitting layer to an electron injecting layer or an electron injecting material, and having excellent thin film-formability is preferable as a hole injecting material. Specific examples of the compound include, but not limited to, a phthalocyanine derivative, a naphthalocyanine derivative, a porphyrin derivative, oxazole, oxadiazole, triazole, imidazole, imidazolone, imidazolethione, pyrazoline, pyrazolone, tetrahydroimidazole, oxazole, oxadiazole, hydrazone, acylhydrazone, polyarylalkane, stilbene, butadiene, benzidine type triphenylamine, styrylamine type triphenylamine, diamine type triphenylamine, derivatives thereof, and polymer materials such as polyvinyl carbazole, polysilane, and a conductive polymer.

Of the hole injecting materials that can be used in the organic EL device of the present invention, additional effective hole injecting materials are an aromatic tertiary amine derivative and a phthalocyanine derivative.

Examples of the aromatic tertiary amine derivative include, but not limited to, triphenylamine, tritolylamine, tolyldiphenylamine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)-phenanthrene-9,10-diamine, N,N-bis(4-di-4- tolylaminophenyl)-4-phenyl-cyclohexane, and an oligomer or a polymer having those aromatic tertiary amine skeletons.

Examples of the phthalocyanine (Pc) derivative include, but not limited to, phthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc, and GaPc-O—GaPc, and naphthalocyanine derivatives.

In addition, the organic EL device of the present invention is preferably formed of a layer containing each of those aromatic tertiary amine derivatives and/or each of phthalocyanine derivatives, for example, the hole transporting layer or the hole injecting layer between the light emitting layer and the anode.

A compound having an ability of transporting electrons, having electron injection efficiency from a cathode and excellent electron injection efficiency to a light emitting layer or a light emitting material, preventing the migration of an exciton generated in the light emitting layer to the hole injecting layer, and having excellent thin film-formability is preferable as an electron injecting material. Specific examples of the compound include fluorenone, anthraquinodimethane, diphenoquinone, thiopyrane-dioxide, oxazole, oxadiazole, triazole, imidazole, perylene-tetracarboxylic acid, fluorenylidenemethane, anthraquinodimethane, anthrone, and derivatives thereof, but the compound is not limited thereto. In addition, an electron-accepting substance can be added to the hole injecting material or an electron-donating substance can be added to the electron injecting material to thereby sensitize the hole injecting material or the electron injecting material, respectively.

In the organic EL device of the present invention, additional effective electron injecting materials are a metal complex compound and a nitrogen-containing five-membered ring derivative.

Examples of the metal complex compound include, but not limited to, 8-hydroxyquinolinatolithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chloro-gallium, bis(2-methyl-8-quinolinato)(o-cresolato)gallium, bis(2-methyl-8-quinolinato)(1-naphtholato)aluminum, and bis(2-methyl-8-quinolinato)(2-naphtholato)gallium.

Examples of the preferred nitrogen-containing five-membered derivative include an oxazole derivative, a thiazole derivative, an oxadiazole derivative, a thiadiazole derivative, and a triazole derivative. Specific examples of the derivative include, but not limited to, 2,5-bis(1-phenyl)-1,3,4-oxazole, dimethylPOPOP, 2,5-bis(1-phenyl)-1,3,4-thiazole, 2,5-bis(1-phenyl)-1,3,4-oxadiazole, 2-(4'-t-butylphenyl)-5-(4"-biphenyl)-1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-t-butylbenzene], 2-(4'-t-butylphenyl)-5-(4"-biphenyl)-1,3,4-thiadiazole, 2,5-bis(1-naphthyl)-1,3,4-thiadiazole, 1,4-bis[2-(5-phenylthiadiazolyl)]benzene, 2-(4'-t-butylphenyl)-5-(4"-biphenyl)-1,3,4-triazole, 2,5-bis(1-naphthyl)-1,3,4-triazole, and 1,4-bis[2-(5-phenyltriazolyl)]-benzene.

In the organic EL device of the present invention, in addition to the aromatic amine derivative selected from the general formulae (1) to (7), at least one kind of a light emitting material, a doping material, a hole injecting material, and an electron injecting material may be incorporated into any one of the organic thin film layers, especially, the light emitting layers. In addition, the surface of the organic EL device obtained according to the present invention can be provided with a protective layer, or the entire device can be protected with silicone oil, a resin, or the like with a view to improving the stability of the device against temperature, humidity, an atmosphere, or the like.

A conductive material having a work function larger than 4 eV is suitably used in the anode of the organic EL device. Examples of an available conductive material include: carbon, aluminum, vanadium, iron, cobalt, nickel, tungsten, silver, gold, platinum, and palladium, and alloys thereof; metal oxides such as tin oxide and indium oxide to be used in an ITO substrate and an NESA substrate; and organic conductive resins such as polythiophene and polypyrrole. A conductive substance having a work function smaller than 4 eV is suitably used in the cathode of the device. Examples of an available conductive substance include, but not limited to, magnesium, calcium, tin, lead, titanium, yttrium, lithium, ruthenium, manganese, aluminum, and lithium fluoride, and alloys thereof. Representative examples of the alloys include, but not limited to, a magnesium/silver alloy, a magnesium/indium alloy, and a lithium/aluminum alloy. A ratio between the components of an alloy is controlled depending on, for example, the temperature of a deposition source, an atmosphere, and the degree of vacuum, and is selected to be an appropriate ratio. Each of the anode and the cathode may be formed in a layer constitution having two or more layers if needed.

It is desirable that at least one surface of the organic EL device is sufficiently transparent in the luminous wavelength region of the device so that the device can efficiently emit light. A substrate is also desirably transparent. A transparent electrode is formed by any one of the above conductive materials, and is set by a method such as deposition or sputtering in such a manner that desired transparency is secured. The light transmittance of an electrode on a light emitting surface is desirably 10% or more. The substrate is not limited as long as it has mechanical strength, thermal strength, and transparency. Examples of the substrate include a glass substrate and a transparent resin film. Examples of the transparent resin film include polyethylene, an ethylene-vinyl acetate copolymer, an ethylene-vinyl alcohol copolymer, polypropylene, polystyrene, polymethyl methacrylate, polyvinyl chloride, polyvinyl alcohol, polyvinyl butyral, nylon, polyether ether ketone, polysulfone, polyether sulfone, a tetrafluoroethylene-perfluoroalkyl vinyl ether copolymer, polyvinyl fluoride, a tetrafluoroethylene-ethylene copolymer, a tetrafluoroethylene-hexafluoropropylene copolymer, polychlorotrifluoroethylene, polyvinylidene fluoride, polyester, polycarbonate, polyurethane, polyamide, polyether imide, polyimide, and polypropylene.

Any one of: dry film forming methods such as vacuum deposition, sputtering, plasma, and ion plating; and wet film forming methods such as spin coating, dipping, and flow coating is applicable to the formation of each layer of the organic EL device according to the present invention. The thickness of each layer is not particularly limited, but must be set to an appropriate thickness. An excessively large thickness requires an increased applied voltage for obtaining certain optical output, resulting in poor efficiency. An excessively small thickness causes a pin hole or the like, so sufficient emission luminance cannot be obtained even when an electric field is applied. In general, the thickness is in the range of preferably 5 nm to 10 µm, or more preferably 10 nm to 0.2 µm.

In the case of a wet film forming method, a material of which each layer is formed is dissolved or dispersed into an appropriate solvent such as ethanol, chloroform, tetrahydrofuran, or dioxane, to thereby form a thin film. At that time, any one of the above solvents may be used. In addition, an appropriate resin or additive may be used in each of the organic thin film layers for, for example, improving film formability or preventing a pin hole in the layer. Examples of an available resin include: insulating resins such as polystyrene, polycarbonate, polyacrylate, polyester, polyamide, polyurethane, polysulfone, polymethyl methacrylate, polymethyl acrylate, and cellulose, and copolymers thereof; photoconductive resins such as poly-N-vinylcarbazole and polysilane; and conductive resins such as polythiophene and polypyrrole. Examples of the additive include an antioxidant, a UV absorber, and a plasticizer.

As described above, an organic EL device having a long lifetime and high luminous efficiency can be obtained by using the aromatic amine derivative of the present invention in the organic thin film layer of the organic EL device.

The organic EL device of the present invention can find use in applications including: a flat luminous body such as the flat panel display of a wall hanging television; a light source for the backlight, meters, or the like of a copying machine, a printer, or a liquid crystal display; a display panel; and a signal lamp. In addition, the material of the present invention can be used in not only the field of an organic EL device but also the fields of an electrophotographic photosensitive member, a photoelectric conversion element, a solar cell, and an image sensor.

EXAMPLES

Next, the present invention will be described in more detail by way of examples.

Synthesis Example 1

Synthesis of Compound (D-66)

In a stream of argon, 4.0 g (10 mmol) of 3,7-di-t-butyl-1,5-dibromonaphthalene, 6.7 g (25 mmol) of 2-dinaphthylamine, 0.03 g (1.5 mol %) of palladium acetate, 0.06 g (3 mol %) of tri-t-butylphosphine, 2.4 g (25 mmol) of t-butoxysodium, and 100 mL of dry toluene were added to a 300-mL three-necked flask provided with a cooling pipe, and then the whole was stirred under heat at 100° C. overnight. After the completion of the reaction, the precipitated crystal was taken by filtration and washed with 50 mL of toluene and 100 mL of methanol, whereby 6.3 g of a pale yellow powder were obtained. The powder was identified as Compound (D-66) (in 82% yield) by NMR spectroscopy (FIG. 1) and field desorption mass spectroscopy (FD-MS).

A DRX500 manufactured by Buker was used in NMR.
[Maximum absorption wavelength 350 nm, maximum fluorescence wavelength 430 nm (toluene solution)]

Synthesis Example 2

Synthesis of Compound (D-142)

Figure 2:
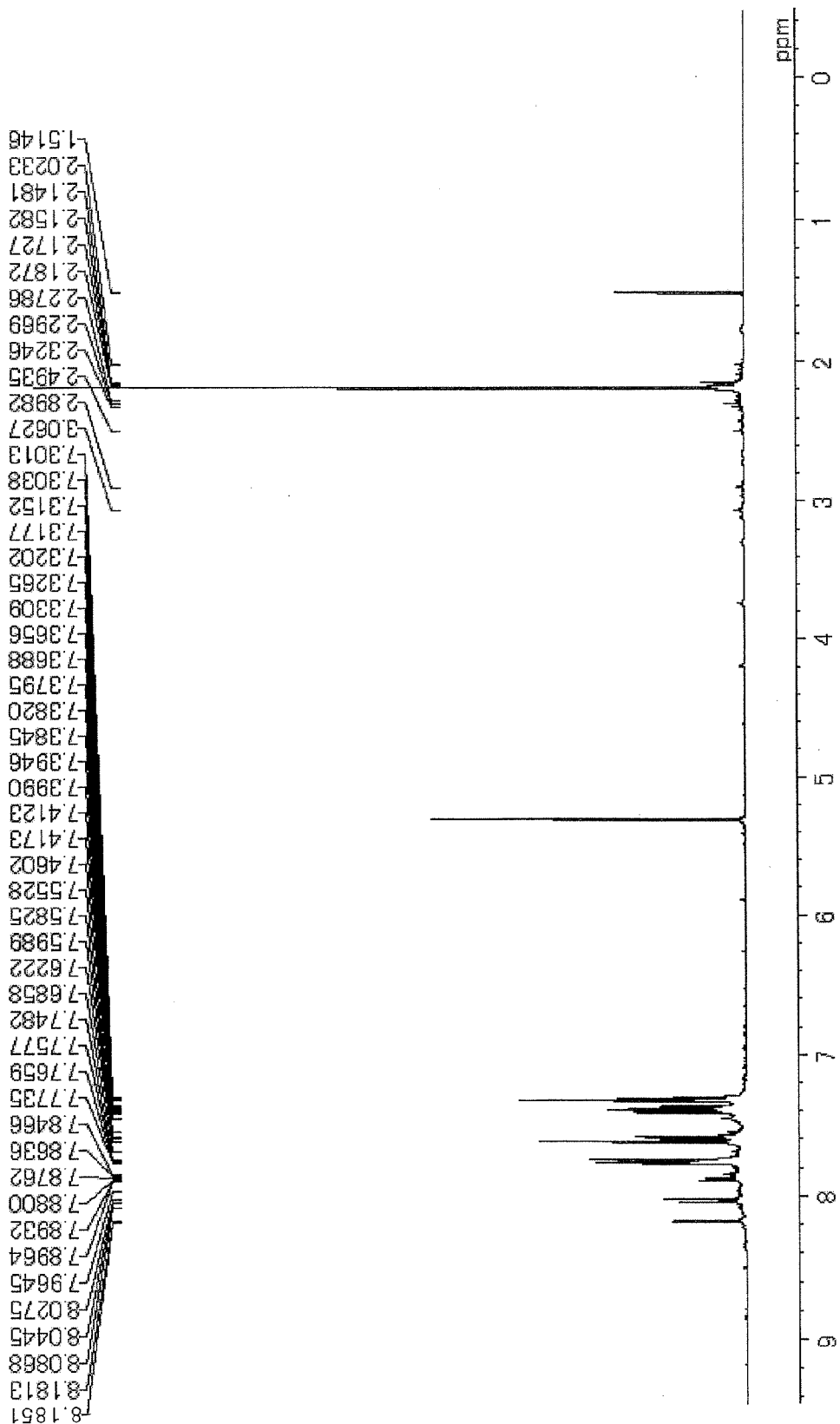
FIG. 2 is a view showing the NMR spectrum of Compound (D-142) as the aromatic amine derivative of the present invention.

In a stream of argon, 4.9 g (10 mmol) of 3,7-di(3,5-dimethylphenyl-1,5-dibromonaphthalene, 6.7 g (25 mmol) of 2-dinaphthylamine, 0.03 g (1.5 mol %) of palladium acetate, 0.06 g (3 mol %) of tri-t-butylphosphine, 2.4 g (25 mmol) of t-butoxysodium, and 100 mL of dry toluene were added to a 300-mL three-necked flask provided with a cooling pipe, and then the whole was stirred under heat at 100° C. overnight. After the completion of the reaction, the precipitated crystal was taken by filtration and washed with 50 mL of toluene and 100 mL of methanol, whereby 8.2 g of a pale yellow powder were obtained. The powder was identified as Compound (D-142) (in 94% yield) by NMR spectroscopy (FIG. 2) and FD-MS.
[Maximum absorption wavelength 353 nm, maximum fluorescence wavelength 420 nm (toluene solution)]

Synthesis Example 3

Synthesis of Compound (D-135)

Figure 3:
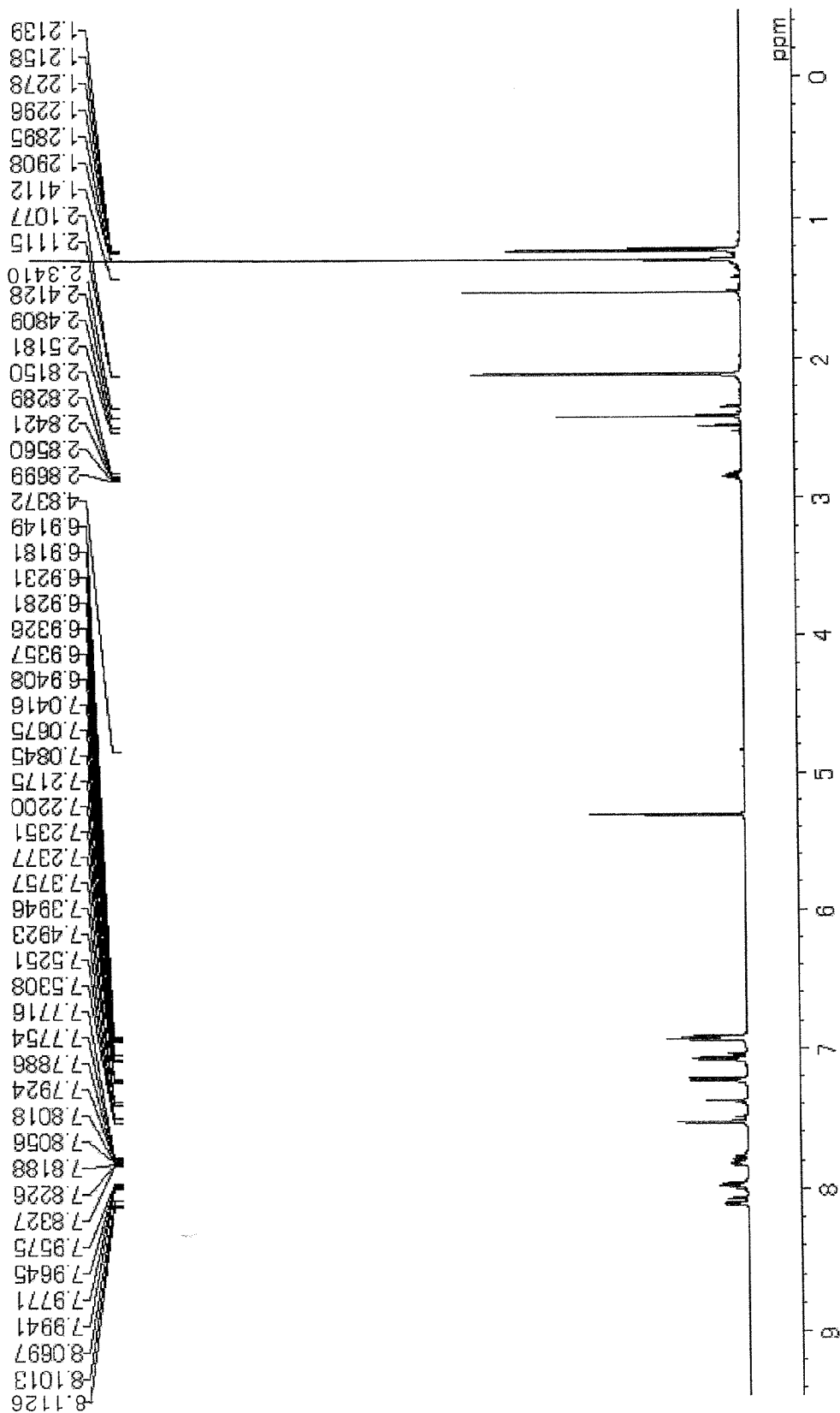
FIG. 3 is a view showing the NMR spectrum of Compound (D-135) as the aromatic amine derivative of the present invention.

In a stream of argon, 4.9 g (10 mmol) of 3,7-di(3,5-dimethylphenyl)-1,5-dibromonaphthalene, 6.7 g (25 mmol) of 4-isopropylphenyl-4'-t-butylphenylamine, 0.03 g (1.5 mol %) of palladium acetate, 0.06 g (3 mol %) of tri-t-butylphosphine, 2.4 g (25 mmol) of t-butoxysodium, and 100 mL of dry toluene were added to a 300-mL three-necked flask provided with a cooling pipe, and then the whole was stirred under heat at 100° C. overnight. After the completion of the reaction, the precipitated crystal was taken by filtration and washed with 50 mL of toluene and 100 mL of methanol, whereby 7.4 g of a pale yellow powder were obtained. The powder was identified as Compound (D-135) (in 85% yield) by NMR spectroscopy (FIG. 3) and FD-MS.
[Maximum absorption wavelength 349 nm, maximum fluorescence wavelength 415 nm (toluene solution)]

Example 1

Production of Organic EL Device

A transparent electrode composed of an indium tin oxide and having a thickness of 120 nm was provided on a glass substrate measuring 25 mm wide by 75 mm long by 1.1 mm thick. The glass substrate was washed by being irradiated with ultraviolet light and ozone, and was then placed in a vacuum vapor deposition device.

First, N',N'''-bis[4-(diphenylamino)phenyl]-N',N'''-diphenylbiphenyl-4,4'-diamine was deposited from the vapor to serve as a hole injecting layer having a thickness of 60 nm. After that, N,N,N',N'-tetrakis(4-biphenyl)-4,4'-benzidine was deposited from the vapor onto the layer to serve as a hole transporting layer having a thickness of 20 nm. Next, 10,10'-bis[1,1',4',1'']terphenyl-2-yl-9,9'-bianthracenyl and Compound (D-66) described above were simultaneously deposited from the vapor at a weight ratio of 40:2 to form a light emitting layer having a thickness of 40 nm.

Next, tris(8-hydroxyquinolinato) aluminum was deposited from the vapor to serve as an electron injecting layer having a thickness of 20 nm. Next, lithium fluoride was deposited from the vapor to have a thickness of 1 nm, and then aluminum was deposited from the vapor to have a thickness of 150 nm. The aluminum/lithium fluoride composite layer functions as a cathode. Thus, an organic EL device was produced.

The resultant organic EL device was subjected to a current test. As a result, the device emitted blue light having a current efficiency of 3 cd/A and an emission luminance of 250 cd/m$^2$ at a voltage of 7.0 V and a current density of 10 mA/cm$^2$. In addition, the device was subjected to a DC continuous current test with its initial luminance set to 1,000 cd/m$^2$. As a result, the device had a half-lifetime of 1,200 hours.

Example 2

Production of Organic EL Device

An organic EL device was produced in the same manner as in Example 1 except that Compound (D-142) was used instead of Compound (D-66).

The resultant organic EL device was subjected to a current test. As a result, the device emitted blue light having a current efficiency of 2.8 cd/A and an emission luminance of 280 cd/m² at a voltage of 7.5 V and a current density of 10 mA/cm². In addition, the device was subjected to a DC continuous current test with its initial luminance set to 1,000 cd/m². As a result, the device had a half-lifetime of 1,000 hours.

Comparative Example 1

An organic EL device was produced in the same manner as in Example 1 except that 1,5-bis(2-naphthylamino)naphthalene was used instead of Compound (D-66).

The resultant organic EL device was subjected to a current test. As a result, the device emitted blue light having a current efficiency of 1.0 cd/A and an emission luminance of 100 cd/m² at a voltage of 7.5 V and a current density of 10 mA/cm². In addition, the device was subjected to a DC continuous current test with its initial luminance set to 1,000 cd/m². As a result, the device had a half-lifetime of 200 hours, which was short.

The foregoing results show that, when a compound in which a diaminonaphthalene skeleton has no substituent is used as a material for an organic EL device, the molecules of the compound associate with each other, with the result that the wavelength of the luminescent color of the device is lengthened, and the current efficiency, emission luminance, and lifetime of the device deteriorate.

INDUSTRIAL APPLICABILITY

As described above in detail, the organic EL device using the aromatic amine derivative represented by any one of the general formulae (1) to (7) of the present invention has high emission luminance and high luminous efficiency, hardly deteriorates even after long-term use, and has a long lifetime. Therefore, the organic EL device is extremely useful as an organic EL device having high practical performance.

The invention claimed is:
1. An aromatic amine derivative represented by the following formula (1):

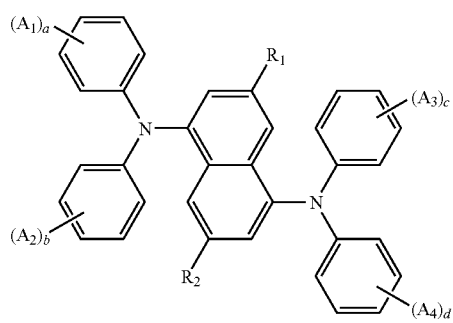

(1)

wherein:
$R_1$ and $R_2$ each independently represents a substituted or unsubstituted aryl group having 5 to 50 carbon atoms or a substituted or unsubstituted cycloalkyl group having 3 to 50 carbon atoms;

$A_1$ to $A_4$ each independently represents a hydrogen atom, a substituted or unsubstituted aryl group having 5 to 50 carbon atoms, a substituted or unsubstituted aralkyl group having 1 to 50 carbon atoms, a substituted or unsubstituted cycloalkyl group having 3 to 50 carbon atoms, a substituted or unsubstituted alkoxyl group having 1 to 50 carbon atoms, a substituted or unsubstituted aryloxy group having 5 to 50 carbon atoms, a substituted or unsubstituted heterocyclic group having 5 to 50 carbon atoms, or a halogen atom; and a to d each independently represents an integer of 0 to 5, and, when each one of a to d represents 2 or more, $A_1$s, $A_2$s, $A_3$s, or $A_4$s may be identical to or different from each other, and $A_1$ and $A_2$, or $A_3$ and $A_4$ may be coupled with each other to form a saturated or unsaturated ring, provided that a derivative wherein a substituent in each group represented by any one of $A_1$ to $A_4$ comprising a group containing a vinyl group is excluded, and a derivative wherein each of $A_1$ to $A_4$ represents a hydrogen atom is excluded.

2. An aromatic amine derivative represented by the following formula (2):

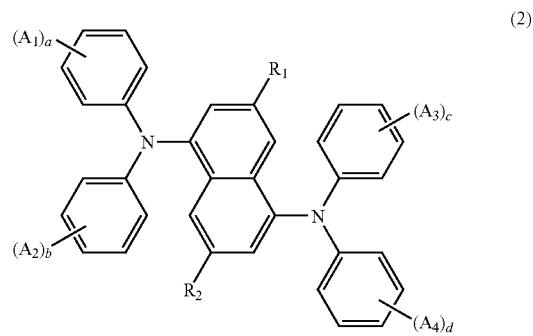

(2)

wherein:
$R_1$ and $R_2$ each independently represents a substituted or unsubstituted aryl group having 5 to 50 carbon atoms or a substituted or unsubstituted cycloalkyl group having 3 to 50 carbon atoms;

$A_1$ to $A_4$ each independently represents a hydrogen atom, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 3 to 50 carbon atoms, a substituted or unsubstituted alkoxyl group having 1 to 50 carbon atoms, a substituted or unsubstituted aryloxy group having 5 to 50 carbon atoms, a substituted or unsubstituted heterocyclic group having 5 to 50 carbon atoms, or a halogen atom; and a to d each independently represents an integer of 0 to 5, and, when each one of a to d represents 2 or more, $A_1$s, $A_2$s, $A_3$s, or $A_4$s may be identical to or different from each other, and $A_1$ and $A_2$, or $A_3$ and $A_4$ may be coupled with each other to form a saturated or unsaturated ring, provided that a derivative wherein a substituent in each group represented by any one of $A_1$ to $A_4$ comprising a group containing a vinyl group is excluded, and at least one of $A_1$ to $A_4$ represents a substituted or unsubstituted, secondary or tertiary alkyl group having 3 to 10 carbon atom.

3. An aromatic amine derivative represented by the following formula (3):

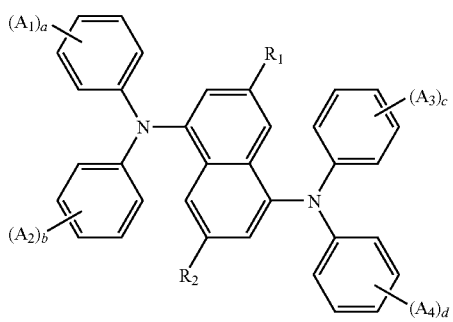

wherein:
- $R_1$ and $R_2$ each independently represents a substituted or unsubstituted aryl group having 5 to 50 carbon atoms or a substituted or unsubstituted cycloalkyl group having 3 to 50 carbon atoms;
- $A_1$ to $A_4$ each independently represents, a substituted or unsubstituted alkyl group having 1 to 50 carbon atoms, a substituted or unsubstituted aryl group having 5 to 50 carbon atoms, a substituted or unsubstituted aralkyl group having 1 to 50 carbon atoms, a substituted or unsubstituted cycloalkyl group having 3 to 50 carbon atoms, a substituted or unsubstituted alkoxyl group having 1 to 50 carbon atoms, a substituted or unsubstituted aryloxy group having 5 to 50 carbon atoms, a substituted or unsubstituted heterocyclic group having 5 to 50 carbon atoms, or a halogen atom; and
- a to d each independently represents an integer of 2 to 5, and, when each one of a to d represents 2 or more, $A_1$s, $A_2$s, $A_3$s, or $A_4$s may be identical to or different from each other, and $A_1$ and $A_2$, or $A_3$ and $A_4$ may be coupled with each other to form a saturated or unsaturated ring, provided that a derivative wherein a substituent in each group represented by any one of $A_1$ to $A_4$ comprising a group containing a vinyl group is excluded.

4. An organic electroluminescence device comprising an organic thin film layer composed of one or more layers including at least a light emitting layer and interposed between a cathode and an anode, wherein at least one layer of the organic thin film layer comprises the aromatic amine derivative according to claim 1 alone or as a component of a mixture.

5. The organic electroluminescence device according to claim 4, wherein the at least one layer of the organic thin film layer which comprises the aromatic amine derivative is present between the anode and the light emitting layer.

6. The organic electroluminescence device according to claim 4, wherein the light emitting layer comprises the aromatic amine derivative, and a content of the aromatic amine derivative is from 0.1 to 20 mass %.

7. A doping material for an organic electroluminescence device, which comprises the aromatic amine derivative according to claim 1.

8. An organic electroluminescence device comprising an organic thin film layer composed of one or more layers including at least a light emitting layer and interposed between a cathode and an anode, wherein at least one layer of the organic thin film layer comprises the aromatic amine derivative according to claim 2 alone or as a component of a mixture.

9. The organic electroluminescence device according to claim 8, wherein the at least one layer of the organic thin film layer which comprises the aromatic amine derivative is present between the anode and the light emitting layer.

10. The organic electroluminescence device according to claim 8, wherein the light emitting layer comprises the at least one layer of the organic thin film layer which comprises the aromatic amine derivative, and a content of the aromatic amine derivative is from 0.1 to 20 mass %.

11. A doping material for an organic electroluminescence device, which comprises the aromatic amine derivative according to claim 2.

12. An organic electroluminescence device comprising an organic thin film layer comprising one or more layers including at least a light emitting layer and interposed between a cathode and an anode, wherein at least one layer of the organic thin film layer comprises the aromatic amine derivative according to claim 3 alone or as a component of a mixture.

13. The organic electroluminescence device according to claim 12, wherein the at least one layer of the organic thin film layer which comprises the aromatic amine derivative is present between the anode and the light emitting layer.

14. The organic electroluminescence device according to claim 12, wherein the light emitting layer comprises the at least one layer of the organic thin film layer which comprises the aromatic amine derivative, and a content of the aromatic amine derivative is from 0.1 to 20 mass %.

15. A doping material for an organic electroluminescence device, which comprises the aromatic amine derivative according to claim 3.

* * * * *